(12) United States Patent
Almen

(10) Patent No.: US 7,460,899 B2
(45) Date of Patent: Dec. 2, 2008

(54) APPARATUS AND METHOD FOR MONITORING HEART RATE VARIABILITY

(75) Inventor: Adam J. Almen, Minneapolis, MN (US)

(73) Assignee: Quiescent, Inc., Minneapolis, MN (US)

( * ) Notice: Subject to any disclaimer, the term of this patent is extended or adjusted under 35 U.S.C. 154(b) by 31 days.

(21) Appl. No.: 11/067,168

(22) Filed: Feb. 25, 2005

(65) Prior Publication Data

US 2005/0177051 A1 Aug. 11, 2005

Related U.S. Application Data

(63) Continuation-in-part of application No. 10/829,544, filed on Apr. 22, 2004.

(60) Provisional application No. 60/464,762, filed on Apr. 23, 2003.

(51) Int. Cl.
*A61B 5/04* (2006.01)
*A61B 5/02* (2006.01)
*G08B 23/00* (2006.01)

(52) U.S. Cl. .................. 600/509; 600/519; 600/481; 340/575

(58) Field of Classification Search ............... 600/515, 600/519, 520, 481, 483; 128/897, 898; 340/575; 345/573.7
See application file for complete search history.

(56) References Cited

U.S. PATENT DOCUMENTS

| 4,570,637 | A | 2/1986 | Gomes et al. |
| 4,938,228 | A | 7/1990 | Righter et al. |

(Continued)

FOREIGN PATENT DOCUMENTS

WO   WO 00/44274   8/2000

OTHER PUBLICATIONS

Effect of position on sleep, heart rate variability, and QT interval in preterm infants at 1 and 3 months' corrected age—sudden infant death syndrome, Pediatrics, Mar. 2003, Ariagno, et al.

(Continued)

*Primary Examiner*—Kennedy J. Schaetzle
*Assistant Examiner*—Natasha N Patel
(74) *Attorney, Agent, or Firm*—Altera Law Group, LLC

(57) ABSTRACT

A wrist-worn or arm band worn heart rate variability monitor is provided. Heart rate variability ("HRV") refers to the variability of the time interval between heartbeats and is a reflection of an individual's current health status. Over time, an individual may use the results of HRV tests to monitor either improvement or deterioration of specific health issues. Thus, one use of the HRV test is as a medical motivator. When an individual has a poor HRV result, it is an indicator that they should consult their physician and make appropriate changes where applicable to improve their health. If an individual's HRV results deviate significantly from their normal HRV, they may be motivated to consult their physician. In addition, the inventive monitor is capable of monitoring the stages of sleep by changes in the heart rate variability and can record the sleep (or rest) sessions with the resulting data accessible by the user or other interested parties. Alternate embodiments of the invention allow assistance in the diagnosis and monitoring of various cardiovascular and sleep breathing disorders and/or conditions. Other embodiments allow communication with internal devices such as defibrillators or drug delivery mechanisms. Still other embodiments analyze HRV data to assist the user in avoiding sleep.

16 Claims, 24 Drawing Sheets

U.S. PATENT DOCUMENTS

| | | | | |
|---|---|---|---|---|
| 5,453,929 | A | * | 9/1995 | Stove .......................... 701/1 |
| 5,738,104 | A | * | 4/1998 | Lo et al. .................... 600/521 |
| 5,749,900 | A | * | 5/1998 | Schroeppel et al. ............ 607/4 |
| 5,876,350 | A | | 3/1999 | Lo et al. |
| 5,928,133 | A | | 7/1999 | Halyak |
| 6,013,009 | A | | 1/2000 | Karkanen |
| 6,126,595 | A | | 10/2000 | Amano et al. |
| 6,265,978 | B1 | * | 7/2001 | Atlas ......................... 340/575 |
| 6,353,396 | B1 | | 3/2002 | Atlas |
| 6,361,502 | B1 | | 3/2002 | Puolakanaho et al. |
| 6,409,675 | B1 | | 6/2002 | Turcott |
| 6,520,905 | B1 | | 2/2003 | Surve et al. |
| 6,553,633 | B1 | | 4/2003 | Rantala |
| 6,571,122 | B2 | * | 5/2003 | Schroeppel et al. ......... 600/515 |
| 6,600,949 | B1 | * | 7/2003 | Turcott ...................... 600/518 |
| 6,889,165 | B2 | | 5/2005 | Lind et al. |
| 7,020,508 | B2 | * | 3/2006 | Stivoric et al. .............. 600/390 |
| 2001/0023320 | A1 | | 9/2001 | Kinnunen et al. |
| 2001/0027266 | A1 | | 10/2001 | Hautala et al. |
| 2001/0056241 | A1 | | 12/2001 | Nissila |
| 2002/0029000 | A1 | | 3/2002 | Ohsaki et al. |

OTHER PUBLICATIONS

Spectral analysis assessment of respiratory sinus arrhythmia in normal infants and infants who subsequently died of sudden infant death syndrome, Pediatric Research, vol. 24, 677-682, copyright 1988 by International Pediatric Research Foundation.

Beat-to-Beat QT Interval Variability, Circulation, 1997; 96: 1557-1565, 1997 American Heart Association, Inc.

Heart Rate and JT Interval During Individual Sleep Stages, G. Varoneckas, D. Zemaityte, Institute Psychophysiology & Rehabilitation, Palanga, Lithuania.

Heart Rate Variabililty During Specific Sleep Stages, Circulation 1995;91: 1918-1922, 1995 American Heart Association, Inc.

Decreased fractal component of human heart rate variability during non-REM sleep, Fumiharu Togo and Yoshiharu Yamamoto, Educational Physiology Laboratory, Graduate School of Education, University of Tokyo, Japan, vol. 280, Issue 1, H17-H21, Jan. 2001.

Effects of Sleep Stage and Age on Short-term Heart Rate Variability During Sleep in Healthy Infants and Children, Chest. 2000;117: 460-466, 2000 American College of Chest Physicians.

Cardiac Autonomic Control in Obstructive Sleep Apnea, American Journal of Respiratory and Critical Care Medicine, Am. J. Respir. Crit. Care Med., vol. 164, No. 5, Sep. 2001, 807-812.

Heart rate variability in patients with sleep-related breathing disorders, AN 97060630; AU Bauer, et al., IN Department of Internal Medicine, University of Bonn, Germany, SO Cardiology. 87(6):492-6, Nov.-Dec. 1996.

Heart Rate Variability, Circulation 1996;93: 1043-1065, 1996 American Heart Association, Inc.

Screening of Obstructive Sleep Apnea Syndrome by Heart Rate Variability Analysis, Roche, et al., 1999 American Heart Association, Inc., pp. 1411-1415.

Heart rate variation in normal infants and victims of the sudden infant death syndrome. Schechtman, et al., Brain Research Institute, University of California, Los Angeles, Early Hum Dev. Jun. 1989;19(3): 167-81.

Heart rate variability in infants with apparent life-threatening events, Katz-Salamon, et al., Department of Woman and Child Health, Karolinska Institute, Stockholm, Sweden.

* cited by examiner

APPARATUS AND METHOD FOR MONITORING HEART RATE VARIABILITY

RELATED APPLICATIONS

This application is a Continuation-In-Part to U.S. patent application Ser. No. 10/829,544, filed Apr. 22, 2004 which claims priority to U.S. provisional patent application No. 60/464,762 filed Apr. 23, 2003.

FIELD OF THE INVENTION

This invention relates generally to monitoring heart rate variability using a wrist worn monitor.

BACKGROUND OF THE PRESENT INVENTION

Heart rate variability refers to the variability of the time interval between heartbeats and may be mathematically defined as the one-sigma standard deviation of the heart rate about the mean heart rate value. A heart rate variability test is a reflection of a person's current health status. By taking heart rate variability tests over time, an individual is able to gauge improvement or deterioration in their health status. Such improvements or deterioration of health may result from a number of sources including, e.g., changes in lifestyle such as smoking cessation, starting an exercise program, surgery recovery, stressor additions or removals, diet changes. Thus, in this context, the HRV test may be used as a medical motivator. The HRV test may also be used as an early indicator diagnostic tool. For example, the HRV test has been demonstrated to have prognostic associations with future coronary disease and events.

Human sleep is described as a succession of recurring stages, including, inter alia, an awake stage, non-REM stages and the REM stage. The awake stage in this context is actually the phase during which a person begins the process of falling asleep. Sleep quality changes with the transition from one sleep stage into another. Significantly for purposes of this invention, the transition from stage to stage is marked with observable, though subtle, changes in bodily function, including heart rate variability.

Analysis of 24-hour HRV typically shows a nocturnal increase in the standard deviation of heart beat intervals. The heart rate is further known to decrease relatively rapidly as a person transitions from the awake stage to the non-REM stages. As the individual eventually transitions from the non-REM sleep stages to REM sleep, the heart rate becomes more erratic and the variability increases. There are several stages of REM sleep, each marked by changes in heart rate variability. The first REM stage typically lasts about 10 minutes, with each recurring REM stage lengthening, with the final stage lasting about one hour. The inventive monitor is capable of detecting the heart rate variability within each sleep stage as well as the transition from one sleep stage to the next, i.e., the transition from awake to non-REM sleep, the transition from non-REM sleep to REM sleep, the completion of an REM sleep stage and subsequent transition to the next REM sleep stage, and the deep slow wave stages (also referred to as delta wave or deep sleep) within non-REM sleep.

In addition, utilization of heart rate, heart rate variability, sleep stage patterns and pattern identification may be used to determine if the user is at risk of suffering from a wide variety of maladies or conditions relating in general to cardiovascular diseases or conditions and sleep breathing disorders or conditions. It would be highly desirable to have a device and method to identify certain maladies, conditions or related events (1) before they occur, (2) during the occurrence of the malady, event or condition, and/or (3) after the malady, event and/or condition has occurred to allow the user and/or health care professional to examine the data, identify the particular malady, event and/or condition, and take appropriate action to correct the problem.

The present invention addresses these concerns.

SUMMARY OF THE PRESENT INVENTION

A wrist-worn or arm band worn heart rate variability monitor is provided. Heart rate variability ("HRV") refers to the variability of the time interval between heartbeats and is a reflection of an individual's current health status. Over time, an individual may use the results of HRV tests to monitor either improvement or deterioration of specific health issues. Thus, one use of the HRV test is as a medical motivator. When an individual has a poor HRV result, it is an indicator that they should consult their physician and make appropriate changes where applicable to improve their health. If an individual's HRV results deviate significantly from their normal HRV, they may be motivated to consult their physician. In addition, the inventive monitor is capable of monitoring the stages of sleep by changes in the heart rate variability and can record the sleep (or rest) sessions with the resulting data accessible by the user or other interested parties. Alternate embodiments of the invention allow assistance in the diagnosis and monitoring of various cardiovascular and sleep breathing disorders and/or conditions. Other embodiments allow communication with internal devices such as defibrillators or drug delivery mechanisms. Still other embodiments analyze HRV data to assist the user in avoiding sleep.

An object of the present invention is to provide a wrist worn heart rate variability monitor capable of performing a heart rate variability test.

Yet another object of the present invention is to provide a wrist worn heart rate variability monitor that allows recording of sleep sessions to determine and improve the quality and duration of the individual's sleep.

Another object of the present invention is to provide a wrist worn or arm worn heart rate variability monitor that is capable of detecting and recording conditions leading to sleep apnea events and the events themselves.

Another object of the present invention is to provide a wrist worn heart rate variability monitor that is capable of detecting SIDS, specifically the proceeding events that lead to SIDS (cardiomyopathy for example).

Another object of the present invention is to provide a wrist worn or arm worn heart rate variability monitor that is capable of communicating with an internal device (defibrillator, drug delivery, sleep/apnea monitor, cardio monitor).

Another object of the present invention is to provide a wrist worn or arm worn heart rate variability monitor that is capable of detecting certain cardiovascular conditions such as arrhythmia and the onset of myocardial infarction and monitoring treatment of same.

Another object of the present invention is to provide a wrist worn or arm worn heart rate variability monitor that is capable of recording heart rate and expressing cardio work load in relation to exercise and calorie expenditure through heart rate data.

Yet another object of the present invention is to provide a wrist worn or arm worn heart rate variability monitor that is capable of monitoring HRV data to assist the user in avoiding sleep.

Still another object of the present invention is to provide a wrist worn or arm worn heart rate variability monitor that is capable of monitoring HRV data to assist the user in a timed rest period or nap.

The foregoing objects and advantages of the invention will become apparent to those skilled in the art when the following detailed description of the invention is read in conjunction with the accompanying drawings and claims. Throughout the drawings, like numerals refer to similar or identical parts.

DETAILED DESCRIPTION OF THE INVENTION

Figure 1:
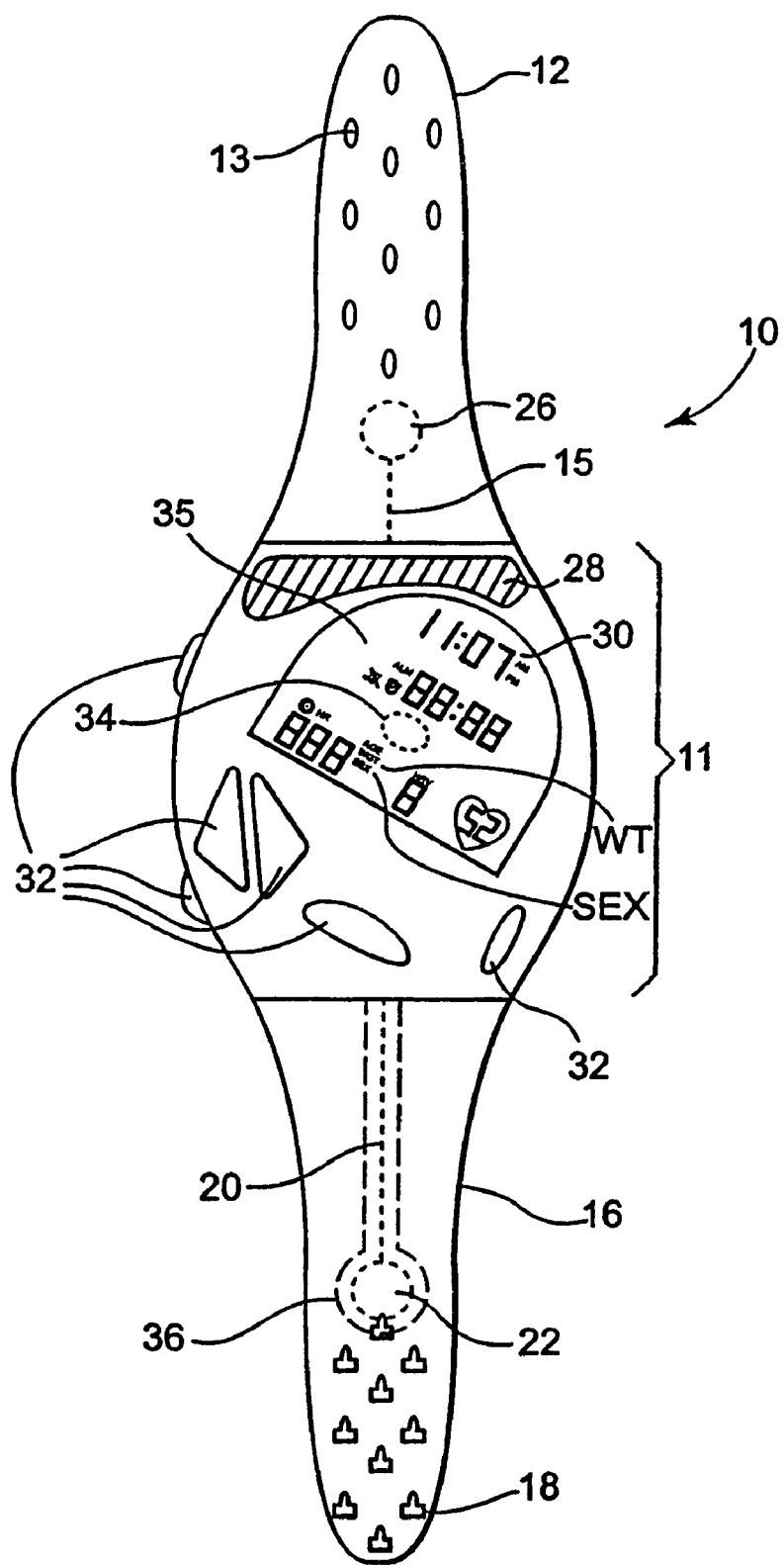
FIG. 1 is a top view of one embodiment of the wrist worn monitor.

A wrist worn heart rate variability monitor for use in the above-mentioned conditions is desirable. Alternatively, the inventive monitor may also be worn on the arm secured by a band encircling the arm. An embodiment of the invention may used to assist the user with a timed nap. The heart rate variability data obtained through the invention is used to determine when the user has achieved sleep or a beneficial level of rest. When the heart rate itself is lowered to a target resting heart rate level, the device starts a timed alarm to wake the user. Both the threshold target heart rate level and the duration of the sleep session may be determined by the user using input buttons to program the device. The user may also choose to be awoken by alarm before, during, or after specific sleep stages, such as REM or deep slow wave sleep.

Another embodiment of the invention may use the heart rate to determine the duration and quality of a sleep session. Users and health professionals may use the device at night in this manner to measure the overall duration of sleep, time spent within a specific sleep stage or stages, to assess the quality of their sleep. The measured data may be stored in the device's memory and accessed either by the user through the device or by the user's physician. The stored information may be related to the physician residing in a remote location via known wired or wireless data transfer techniques. The results may be assessed for quality of sleep by recognizing when the heart rate is above or below the preset threshold target level as well as variations in the intervals between heart beats. Thus, the data may be used to determine whether or not the user is getting quality sleep, or is waking during sleep which is common in persons suffering from sleep apnea and heavy snoring. This information may be used by the user as a motivator to see a physician and/or a sleep specialist. This information is also valuable to the user's physician in determining if treatment is necessary and what type of treatment would be most effective. Subsequent impact of the treatment may also be evaluated using heart rate variability information. The device may be further used in concert with a memory device such as a mini flash drive or memory stick. In this embodiment, the inventive device would communicate with the memory device in ways that are well known in the art and not shown in the Figures. In one such embodiment, the inventive monitor may have a port for communication with the memory device wherein the monitor's memory is transferred to the memory device. The memory device may then be connected to the user's computer for review of the data. Such data may be subsequently provided to the user's health care professional(s) computer for analysis. This data transfer may be accomplished computer-to-computer via the internet or, alternatively, the user may save the data to a computer disk and bring the disk to the health care professional. Further, the user may provide the health care professional with the memory device itself for communication with the health care professional's computer.

Another embodiment may utilize the heart rate to perform a heart rate variability test (HRV). HRV tests are typically performed while the subject is at rest or asleep or may be done over a user's normal 24-hour activities. User's can choose to have an HRV test performed using an input button. An HRV test may be performed in as little as ten seconds, but the longer the test, the more accurate the results. Users can utilize the HRV option while taking a timed nap, during a resting period, or when sleeping at night.

Still another embodiment enables the device to be used in concert with a home's electronics control unit. Many homes are equipped with a controlling computer system. These homes have been referred to as 'smart houses.' The home's controlling computer or electronics control unit manages the functions of the home. These functions may include: television; personal computer; shower; home security system; lights; kitchen appliances; garage door and other functional features of a home. This invention is capable of working in concert with the home's controlling computer system and works to synchronize the home's functions with the homeowner's functions. The user wears the device before bed and when the user's heart rate level and variability reach the threshold level, the wrist worn monitor sends out a signal to the home's controlling computer which then prepares the home for the night, i.e., places the home in 'sleep' mode. This may comprise functions such as shutting lights and televisions off, and ensuring the garage door is down, setting the thermostat at an appropriate temperature for the night, etc. The opposite is done in the morning. When the user's heart rate level and variability rises above the threshold level, the monitor sends a signal to the central home computer to prepare the home for the day, i.e., placing the home in 'awake' mode. Thus, functions such as turning on the lights, shower, coffee maker, alarm are accomplished. In addition to using the heart rate variability of the user to control the features of the home, the monitor may have a button that manually accomplishes the tasks without use of heart rate variability information.

Another embodiment of the device may recognize and/or assist in the diagnosis of the onset of maladies and/or conditions that cause Sudden Infant Death Syndrome (SIDS) and/or heart rate variability and sleep stage patterns comprising events associated with SIDS. Such recognition may occur proactively or predictively, concurrent with the malady or event, and/or retrospectively. In this embodiment the device may utilize heart rate, heart rate variability and sleep stage patterns and pattern identification to determine if the user is at risk of suffering from SIDS. In this embodiment, thresholds and algorithms are applied to the heart rate for identification of events placing the user at risk of SIDS or recognition of when a SIDS even is occurring or has occurred. Pattern recognition and pre-event milestone recognition allow the device to alert the user, parent, or health care professional to an upcoming event or an event in progress. As an example, cardiomyopathy or long Q-T syndrome may be identified by the inventive monitor, with subsequent alerting of the user or an outside party (in this case perhaps the infant's parents or healthcare professional) of the event. This may assist in a preliminary diagnosis so that proper steps toward treatment may begin. The devices alarm system may give parents or the user a chance to prevent the event from happening or continuing.

Another embodiment of the device may assist in the recognition of sleep stages and sleep disorders. The device is able to determine the user's sleep stage and abnormalities, REM, non-REM, deep slow wave sleep, and sleep apnea syndrome through HRV, heart rate, algorithms, and the programming of patterns for recognition. Other sleep disorders may be recognized based on data and patterns recognized by the device and health care professionals reviewing the data and patterns as well as the user disseminating the information to determine a sleep problem. Various embodiments of the inventive device may incorporate an actigraph, pulse oximetry, and a method for measuring peripheral arterial tone. These additional tools coupled with heart rate variability and heart rate may provide a means of cross referencing and/or secondary information source needed to determine if the user is asleep, experiencing a sleep disorder or other malady or event to assist in providing more accurate information for the user and health care professionals.

With reference to pulse oximetry, an infra-red sensor may be used to obtain or measure the heart rate. Infra-red detection transmits infra-red light through the user's skin which is then reflected back to the sensor. This method picks up the pulsatile flow of blood through local capillaries producing an accurate heart rate measurement. Infra-red detection further allows for the measurement of oxygen levels in the blood. The oxygen levels in the blood are a reflection of respiration and may be used as an indicator of respiratory problems that may result from chronic obstructive pulmonary disease or obstructive sleep apnea by way of example. Those skilled in the art will readily recognize a plurality of diseases or conditions that may be monitored, diagnosed or treated using pulse oximetry and/or oxygen level measurement.

One exemplary condition that may be identified and monitored is sleep apnea. Sleep apnea is a condition whereby afflicted individuals literally stop breathing repeatedly during sleep, often for a minute or longer and as many as hundreds of times during a single night's sleep. Very often individuals with sleep apnea experience disrupted sleep and are prevented from reaching the later stages of sleep, such as REM sleep, which the body requires for rest and replenishment of strength. Heart rate variability data can be used to assist the physician in diagnosing and monitoring the efficacy of treatment regimens for sleep apnea. The inventive monitor may be used to determine whether heart rate variability indicates that sleep is continually interrupted and whether a sufficient amount of REM sleep and deep slow wave sleep is being obtained. In addition to the recognition of sleep apnea events, the inventive monitor provides an overall view of the users sleep and sleep patterns, including the identification of the users sleep stages, stages one through five, allowing the user or health care professionals to identify abnormalities or other sleep disorders.

The device may be outfitted with a transceiver to communicate with internal devices or with external devices. Internal devices such as defibrillators, insulin pumps, drug delivery/pumps, apnea monitors, pulse transmitters, and heart rate monitors (monitoring for abnormalities or cardiac events). In this application the device can be used to display pertinent information for the user as well as transmit information to the internal device. The internal device communicates information to the inventive monitor via the transceiver regarding a significant event. In the case of an internal defibrillator, the significant event may be an impending stimulation from the defibrillator with the option to override the automatic system or delay it. In one embodiment, the inventive monitor's alarm alerts the user of the impending significant event, in the example the defibrillation stimulation. Thus, if the user is driving a car they may choose to delay the stimulation so they can pull over to the side of the road. The user will be alerted by an audible or vibrate alarm to the impending stimulation so they can prepare for it or they can use an input button to delay the stimulation or use an input button to override the stimulation all together so at a later and safer time they can stimulate themselves through an input button on our device. In the case of an insulin pump the user can receive information used for tailoring their diet and activities based on the timing and amount of insulin delivered. Alerting the user of this exemplary significant event, an insulin dosage, can also help the user prepare for the effects of the insulin. The same principles apply for drug delivery/pumps as with insulin pumps.

The user will also be able to easily view information gathered by the internal device on the inventive device's display. The internal device may, in an alternate embodiment be placed into a "decision mode" by an input on our device. The decision mode would prompt the internal device to transmit a signal to the inventive device's transceiver (external) requesting permission before it performed certain significant events such as, delivering a drug or administering stimulation (defibrillator). The internal device would function in its normal role until it is told to ask permission from the external device. The user may grant or deny permission via communication with the internal device using the inventive monitor's transceiver function. The user may also transmit via the monitor's transceiver to the internal device that the significant event may occur, but not until a programmable period of time has passed. The internal device could be equipped with an override function, in case of human error or if it determines that the situation requires its function (stimulation, drug delivery). Such an internal device may further perform a self-test of its systems and vital elements and relay that diagnostic information to the inventive device. Such diagnostic information may be used to alert the user of any potential problems or issues with the internal device requiring attention and/or correction. The inventive device may, using methods described herein, transmit or communicate the internal device's diagnostic information to an appropriate third party such as the user's health care professional or other institution or individual(s) that may be monitoring the internal device.

Using HRV test data, the inventive device may be capable of detecting and/or assisting in diagnosing various heart maladies and/or conditions. Exemplary conditions that may be detected or diagnosed comprise inter alia, cardiovascular disease such as, Adams-Stokes Disease, Aneurysm, Angina Pectoris, Antiphospholipid Syndrome, Aortic Aneurysm, Aortic Regurgitation, Arrhythmias, Atherosclerosis, Atrial Fibrillation, Bacterial Endocarditis, Bundle Branch Block, Cardiomyopathy, Cholesterol, High, Chronic Obstructive Pulmonary Disease, Congestive Heart Failure, Coronary Artery Spasm, Diastolic Dysfunction, First Degree A-V Block, Heart Murmurs, Hypertension, J-Curve Phenomenon, Long Q-T Syndrome, Marfan Syndrome, Mitral Valve and Mitral Valve Prolapse, Pericarditis, Peripheral Vascular Disease, Premature Ventricular Contractions, Raynaud's Phenomenon, Rheumatic Heart Disease/Rheumatic Fever, Silent Ischemia, Ventricular Fibrillation, Wolff-Parkinson-White Syndrome. In addition other forms of congenital heart disease may be identified or assisted in diagnosis by the invention, including, inter alia, Aortic stenosis, Atrial septal defect, Atrioventricular canal defect, Bicuspid aortic valve, Coarctation of the aorta, Ebstein's anomaly, Eisenmenger's complex, Hypoplastic left heart syndrome, Patent ductus arteriosus, Pulmonary stenosis, Pulmonary atresia, Subaortic stenosis, Tetralogy of Fallot, Total anomalous pulmonary venous connection, Transposition of the great arteries, Tricuspid atresia, Truncus arteriosus, and Ventricular septal defect.

In some instances the device can recognize the onset of these events before they come to fruition, this is achieved with pattern recognition and pre-event milestone recognition based on the HRV test results that allow the device to alert the user, parent, or health care professional to an upcoming event or an event in progress. In some instances, the HRV data used to develop prognoses for cardio-related maladies, diseases and/or events may be used in concert with the inventive device's ability to evaluate sleep maladies, conditions and/or events. Health care professionals may then use the two sets of data to inform diagnoses and/or treatment.

For example, when the device identifies an abnormal cardio event or the onset of such an event the alarm can alert the users to take the proper steps, whether that is taking a drug to counteract the event or simply ceasing their current activity. For example, a user may be alerted to abnormal HRV data occurring in the very early stages of a heart attack. The data may also be transferred to the users physician or health care professional so that they may take appropriate action or obtain information that will assist in the diagnosis of any condition that may exist.

Another embodiment of the device may utilize the HRV data to determine the workload placed on the heart. For instance, if an individual is trying to lose weight the workload placed on their heart can be a reflection of their daily habits including exercise. Their heart rate over time can also be used as a marker of their health; resting heart rate and optimal heart rate are often used for such markers. A good example of this application is for obese individuals.

Health-professionals may use the heart rate data to determine if their patient is within their treatment parameters and make recommendations based on the data. For example, patients contemplating beginning an exercise regiment may consult their doctor's prior to beginning. The healthcare professional may evaluate the HRV data obtained from the inventive monitor and gain an understanding about the level of heart functioning and whether there are any potential problems that the healthcare professional may wish to investigate before allowing the patient to begin exercising. The heart rate is also used for those exercising as a reflection of their performance. For example the time spent within their target heart rate zone; cool down heart rate, and resting heart rate. HRV can also be incorporated in this application because of its health reflection attributes.

The present invention is capable of monitoring, recording and analyzing sleep and/or rest sessions. The device monitors an individual's heart rate variability while the user is either at rest or asleep or physically active and records the results for up to 24 hours. The inventive monitor is capable of detecting and measuring the variability of heart rate during the sleep sessions and is further capable of discerning the subtle differences in heart rate variability as the user transitions from one sleep stage to the next. This record is stored in the device's memory and is accessible for review by the user or interested $3^{rd}$ parties such as the user's physician or nurse.

With reference to the accompanying Figures, there is provided a wrist worn heart rate variability monitor 10. Alternatively, the monitor 10 may be worn on the arm using a belt that is well known in the art, thus this embodiment is not shown in the Figures. As shown in FIG. 1, the monitor 10 is comprised of the monitor body 11, wristband B 12 and wristband A 16. The attributes of wristband B 12 will preferably be comprised of securing holes 13, a waking prompt 26 and a wire 15 connecting the waking prompt 26 to the monitor body 11. The attributes of wristband A 16 will preferably be comprised of securing hooks 18, at least one wire 20, sensor A 20 and may include a plastic insert on the back of wristband A. The monitor body 11 will preferably comprise a sensor B 34, display 35, a waking prompt or alarm 26, remote emitter 28, clock 30 and input buttons 32. The monitor may have a plurality of input buttons 32 which collectively make up the input, though one skilled in the art will recognize that more or fewer input buttons 32 may be used to accomplish the desired goals described herein.

Figure 2:
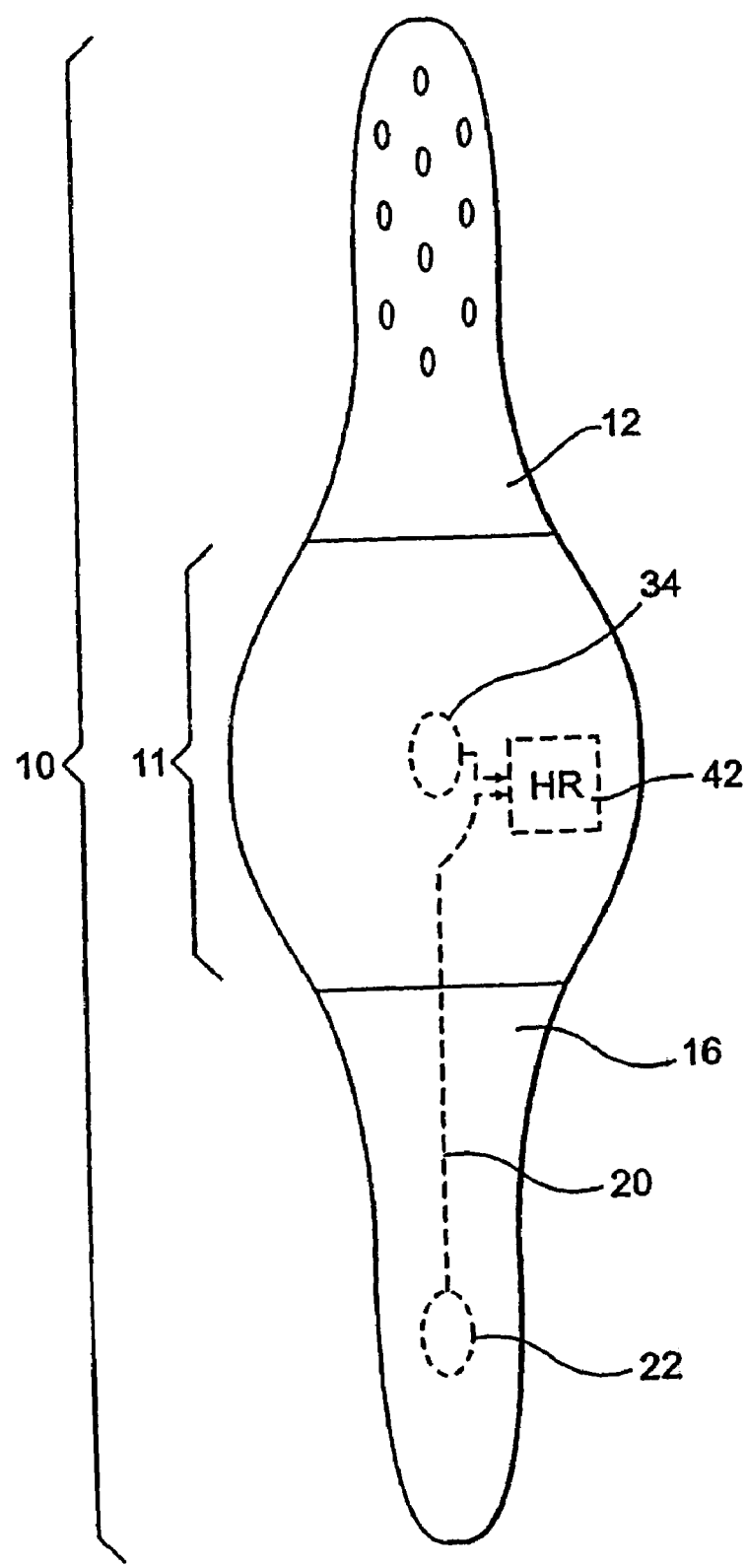
FIG. 2 is a bottom view of one embodiment of the wrist worn monitor with sensor(s) and wires in phantom.

Turning now to FIG. 2, the inventive monitor 10 detects the heart rate using at least one sensor, two sensors 22, 34 are provided in the Figure to illustrate an electrode sensor, although some sensors may only require one sensor to obtain the heart rate. In the case of an electrode sensor as shown, preferably the electrical signals are electrocardiograph (ECG) signals generated by the heart. Thus, in the preferred embodiment, the monitor 10 detects heart rate.

The heart rate sensors 22, 34 are integrated into the monitor. Sensor A 22 is housed in wristband A 16. Heart rate sensor A 22 may partially penetrate the surface of wristband A 16 or may be flush with the surface of wristband A 16. Heart rate sensor A 22 is connected with a wire(s) 20 or fiber optic(s) thread(s) to the applicable unit for measuring the heart rate. These connective wire(s) 20 or thread(s) are housed in wristband A 16 and connect Heart rate sensor A 22 to the monitor body 11 and in turn, to the applicable heart rate measuring device. Heart rate sensor B 34 is disposed on the back surface of the monitor body 11 so that it makes contact with the user's skin when worn. Heart rate sensor B 34 may protrude from the back surface of the monitor body 11 or, alternatively, it may be flush with the back surface of the monitor body 11.

To properly calculate HRV, a medically accurate measure of instantaneous and average heart rate must be determined. To pick up heartbeats, and thus measure the rate, it is contemplated that a variety and/or a plurality of sensors may be advantageously deployed, using optic, pressure, ultrasonic, and, electrical means.

Thus, device may use at least one capacitive micromachined ultrasound transducer, referred to as cMUT's, to obtain heart rate through pulsatile blood flow. A cMUT is also referred to as a capacitive/capacitor microfabricated ultrasonic transducer. The cMUT method of obtaining heart rate is further simplified by known techniques of curving the silicon within the sensor by thinning the silicon, this curvature will allow better contact with the skin and give a more accurate heart rate.

To detect heart beats, a cMUT sensor/device may be used. The cMUT sensor works much the same way as a diagnostic ultrasound transducer, but at much lower power, and with greater accuracy. The cMUT sensor reacts to the pulsatile blood flow sound reflections, typically in the radial artery, by producing an electrical signal on each pulse. This signal is sent to the heart rate computation unit which in turn determines the heart rate of the user. A single cMUT sensor/device may be placed in position 22 or 34, or any other position that will allow the sensor to pick up the heart rate signal. At least one such sensor is employed by the inventive monitor.

Figure 3A:
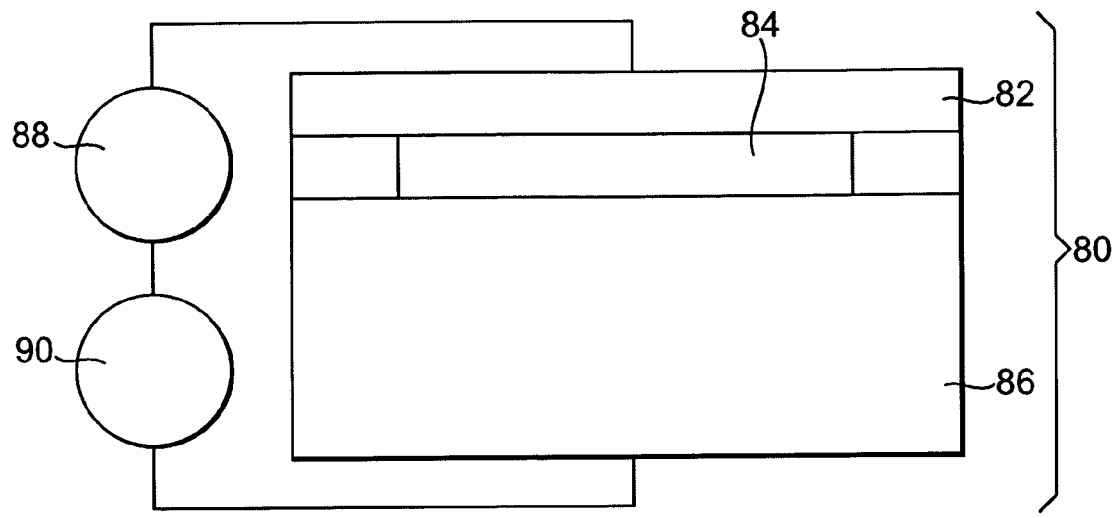
FIG. 3A illustrates a capacitive micromachined ultrasound transducer in a normal state.

FIG. 3A illustrates a cMUT sensor/device 80. To detect heartbeats, a cMUT sensor/device 80 may be used. A single cMUT sensor/device 80 may be placed, e.g., in position 22 or 34 as indicated in FIGS. 1 and 2. However, a plurality of sensors may also be used and the positioning of the at least one sensors to determine the most advantageous detection point or sensor may differ from the illustrated positions. The cMUT sensor works much the same way as a diagnostic ultrasound transducer, but at much lower power, and with greater accuracy. The cMUT reacts to the pulsatile blood flow sound reflections, typically in the radial artery, by producing an electrical signal on each pulse. This signal is sent to the heart rate computation unit that, in turn, determines the heart rate of the user. The cMUT sensor 80 comprises of a silicon nitride membrane and support 82, vacuum gap 84, silicon substrate 86, AC current 88, and DC current 90. FIG. 3A depicts the cMUT sensor 80 in a normal state.

Figure 3B:
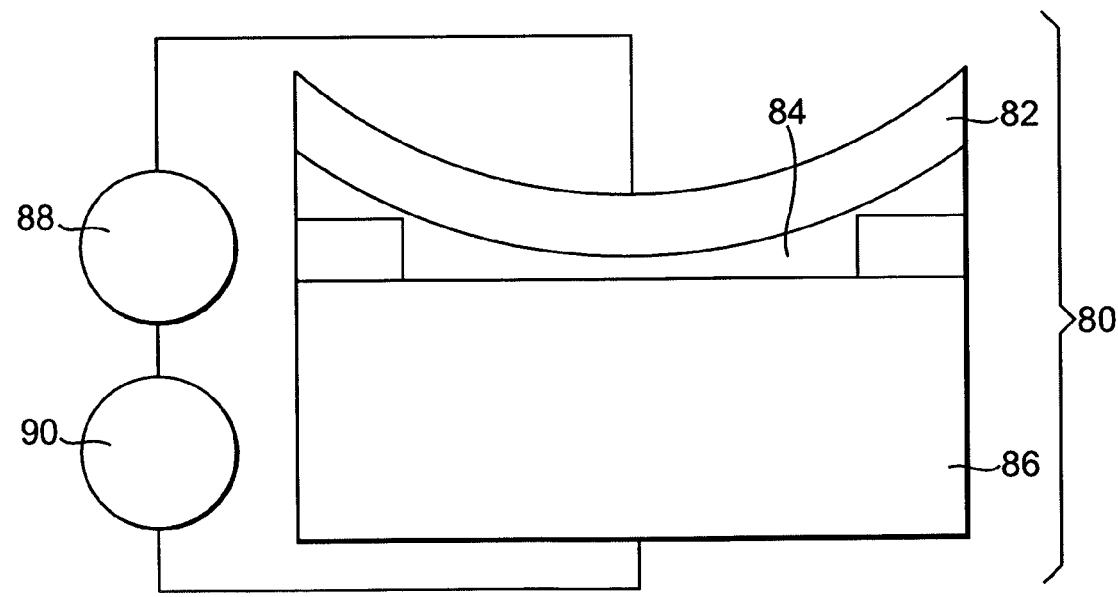
FIG. 3B illustrates a capacitive micromachined ultrasound transducer in a deformed state.

FIG. 3B illustrates the cMUT sensor 80 in a deformed state. In its deformed state the silicon nitride membrane 82 is shown altered from its normal state.

Alternatively, a piezoelectric sensor/device may be used to detect the heart beat, a single piezoelectric sensor/device may be placed in position 22 or 34. However, a plurality of such sensors may be employed and those skilled in the art will readily determine the most advantageous detection point for each sensor used. The piezoelectric sensor reacts to pulsatile blood flow and mechanical aterial forces via deformation of its original shape, thus outputting an electrical signal indicating presence of a heart beat. The piezoelectric sensor detects the pulse from the wrist, typically at the radial artery.

An alternate embodiment that improves upon the above-described piezoelectric sensor technology is commercially available under the trade name Thunder® and is distributed by the Face International Corporation of Norfolk, Va. may be used advantageously as a sensor in the inventive device. The Thunder® sensor/device works on the same principles of a piezoelectric sensor but is typically comprised of layers of stainless steel, aluminum and PZT piezoceramic. This arrangement improves sensitivity, and is useful in smaller signal applications, such as found in infants.

Another sensor embodiment comprises a pressure transducer alternative that uses the piezo electric effect is referred to herein as MEMS (micro electromechanical sensor). MEMS integrate the piezoelectric sensor with sense amplifier electronics onto one slice of silicon. The sensor itself is created by micro-machining a square area out of the center of die via a bulk etching process, thus creating a thin diaphragm within the die which becomes the piezo sensor. The advantage of MEMs sensors is that they are easily fabricated with standard silicon fabrication techniques, making very small, highly integrated, and extremely cost effective.

Other embodiments may use an optical sensor to detect the heart beat and measure heart rate variability, a single optical sensor may be placed in position 22 or 34. However, a plurality of optical sensors may be used and placed by those skilled in the art to determine the most advantageous detection sensory location(s). Optical sensors are well known in the art. One such example may transmit an optical infrared (IR) signal, or other optical signal, to the skin tissue where it may be modified due to refraction, reflection, scattering and absorption. The optical sensor may measure optical variations in tissue characteristics due to subcutaneous blood flow that may correlate with heart rate. Equivalent optical sensors will readily present themselves to those skilled in the art.

A combination of the types of sensors described above may be used. For example, the commonly used electrode sensors, glass filled ABS, coated with Ag/AgCl (resistive type) or a glass thin-films type of capacitive electrode or ohmic contact silver chloride electrode may be used with an optical sensor. A cMUT type of sensor, piezoelectric sensor, electrode sensor, or optical may be used in combination with each other or independent of each other.

Figure 4:
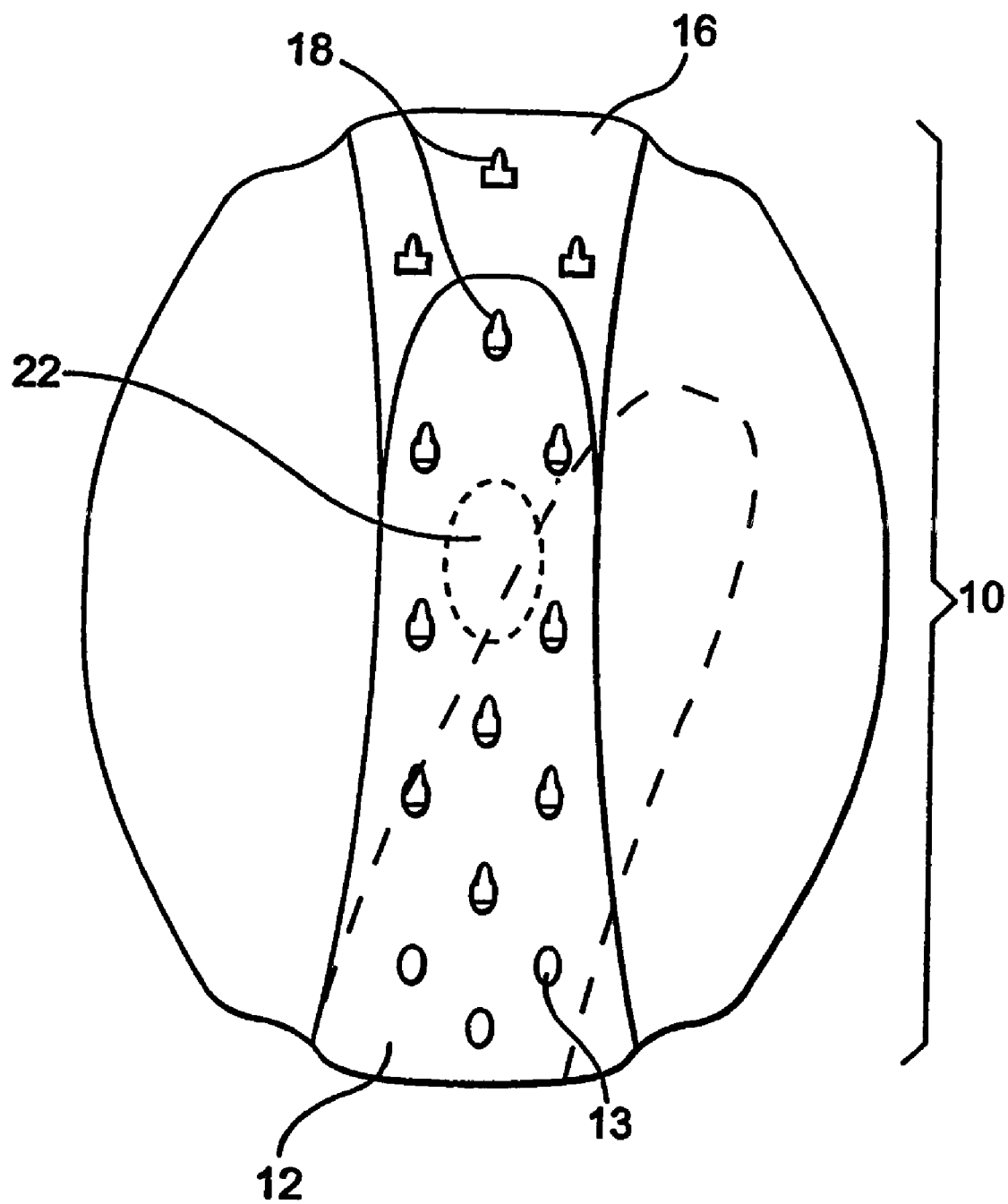
FIG. 4 is a side view of one embodiment of the wrist worn monitor closure.

Referring now to FIG. 4, the monitor 11 is attached to the user's wrist preferably using a system of holes 13 on wristband B 12 and securing hooks 18 on wristband A 16. The pliability of wristband B 12 allows the user to adjust the position of the securing points allowing sensor A 22 in wristband A 16 to have a proper fit and positioning for an accurate heart rate reading and further provides comfort on the user's wrist. Alternatively, the monitor 10 may be attached to the user's wrist by means of Velcro, buckle attachment, clasp, ball and hole, or other methods not shown in the Figures, but that are well known to those skilled in the art.

Figure 5:
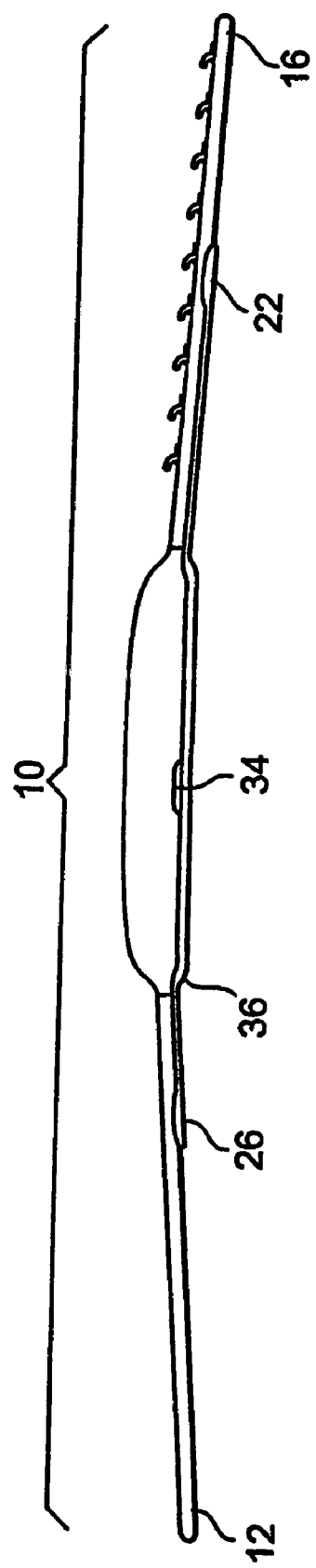
FIG. 5 is a side view of one embodiment of the wrist worn monitor.

Turning now to FIG. 5, the monitor 10 may be largely constructed using technology that is conventional for construction of electronic watches. The monitor 10 will most likely be constructed of different types of plastic that range from rigid to pliable. Wristband B 12 may be made of different material than used in wristband A 16. The material in wristband B 12 may be more pliable than the material in wristband A 16 and vice versa. Such technology is not described herein in detail because it is well known to those skilled in the art.

Figure 6:
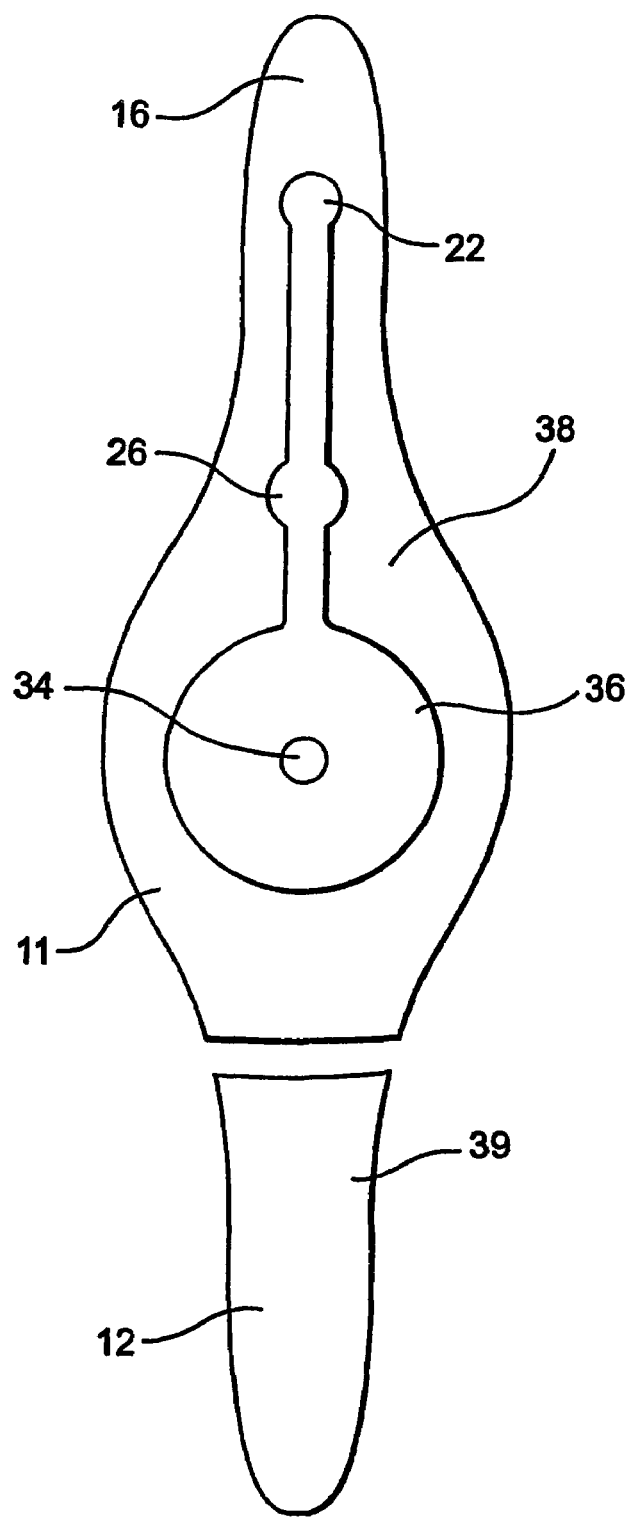
FIG. 6 is a bottom view of the wrist worn monitor illustrating possible two piece manufacture.

As indicated in FIG. 6, the monitor 10 may be made of two pieces. The monitor may be built using several different methods. It may have a pliable piece of plastic 36 that is inserted on the back side of the device sealing sensor A 22 into wristband A 16, sensor B 34 into the monitor body 11 and the waking prompt 26 into wristband B 12. One piece 38 may combine the monitor body 11 and wristband A 16. Wristband A 16 would house both the waking prompt 26 and sensor A 22. The second piece 39 would consist of a wristband B 12 and would be connected to the monitor body 11. The pliable plastic insert 36 may not need to cover sensor B 34. In both of these cases, the pliable plastic insert 36 would cover sensor A 22 and possibly sensor B 34 respective to the use of the insert 36. The connectivity method between wristband B 12 and the monitor body 11 is not discussed further as it is well known to those skilled in the art. Additionally, other common forms of manufacture are not described herein as they are well known to those skilled in the art.

Figure 7:
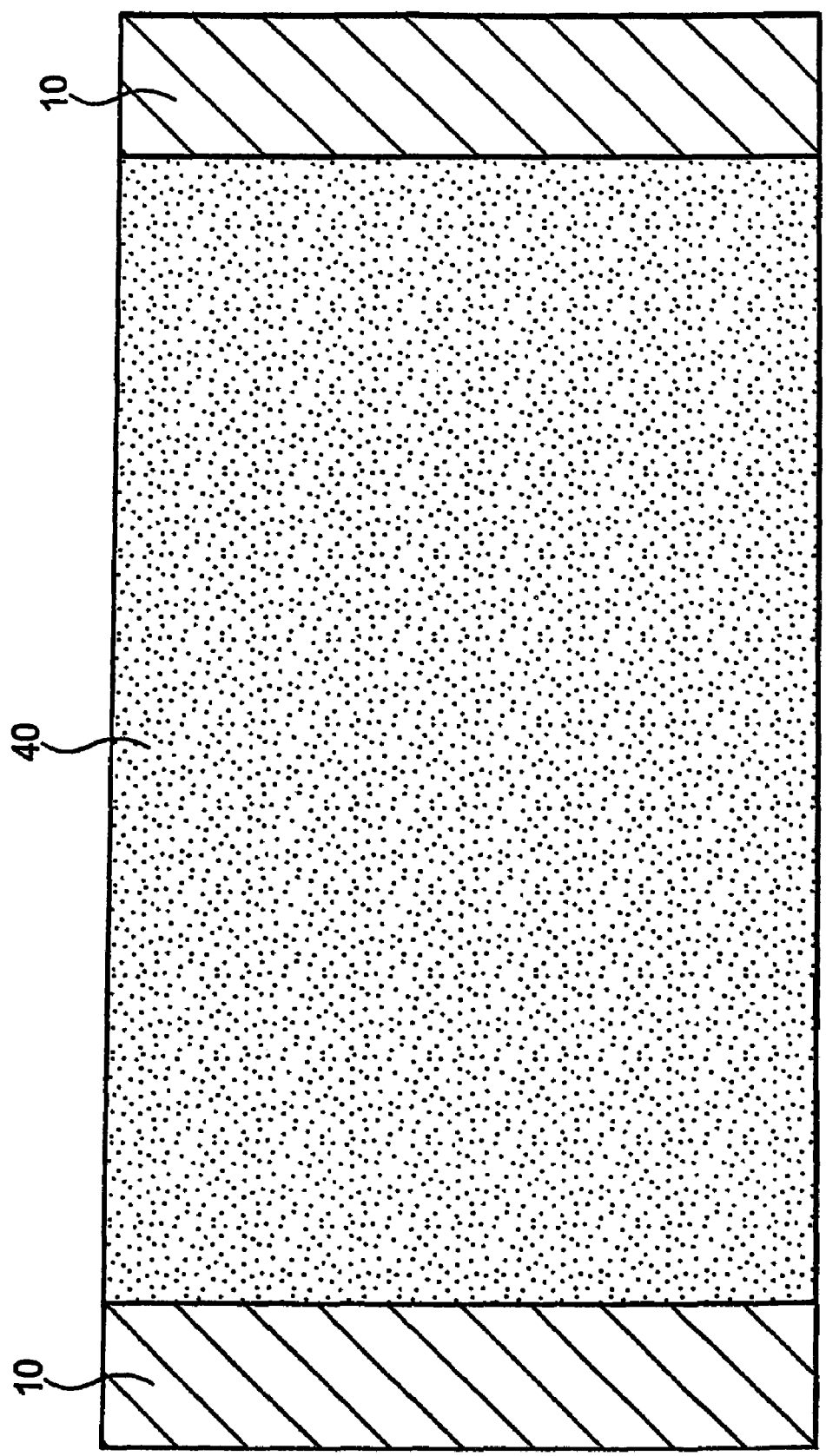
FIG. 7 is a top view of the membrane attachment.

As illustrated in FIG. 7, a conductive membrane 40 may be attached to the back surface of the monitor 10 to increase the electrical conductivity, thus enhancing the monitor's ability to pick up the electrical signals generated by the heart. The membrane 40 may also be attached to the monitor's wristband covering the sensors and having contact with the user's skin. The membrane 40 may be porous and may be used in concert with conductive gels. In this embodiment, the user will place a small amount of gel onto the membrane 40. The membrane will absorb the gel and the conductive properties of the gel will assist the sensors 22, 34 in obtaining more accurate heart rate variability information. Preferably, the membrane 40 will retain the gel for multiple uses, thus eliminating the need for repeated applications of the gel to the membrane 40. The membrane 40 may also be constructed of conductive materials, thus eliminating the need for conductive gel. The membrane 40 will also benefit the fit of the electrode to the user's skin by eliminating or minimizing the space between the electrode or the other above mentioned sensors and the user's skin.

Figure 8:
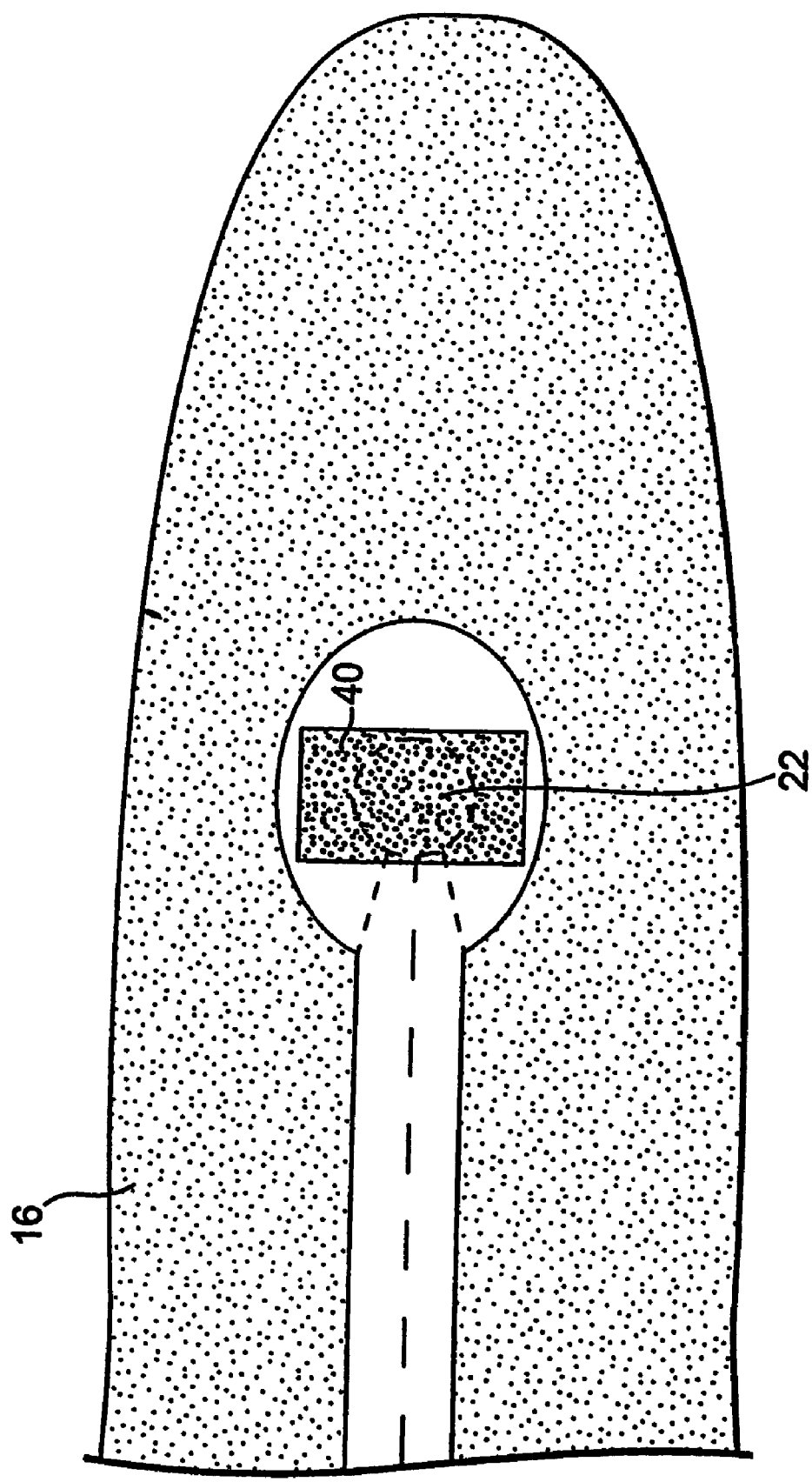
FIG. 8 illustrates the membrane attached to the wrist worn monitor.

FIG. 8 illustrates the preferred embodiment for placement of the conductive membrane 40. The membrane 40 self-adheres to wristband A 16. A portion of wristband A 16 surrounding sensor A 22 will be smoothed out, thus ensuring good adhesion of the membrane 40. The membrane 40 is replaced when necessary by simply removing the used membrane 40 and applying a new membrane 40. One exemplary embodiment for the conductive membrane 40 is 'Metal Rubber' a conductive substance made by NanoSonic, Inc., located in Blacksburg, Va. 'Metal Rubber's' advantage over other membranes is its resiliency to outside substances and neutrality to human skin. The use of 'Metal Rubber' will prolong and protect the sensor without interfering with the sensor, in the case of an electric sensor, the 'Metal Rubber' is conductive and may assist the sensor in its readings or gathering of electrical pulses. The "Metal Rubber' may enclose the sensor (s) and the transmitter(s) used with a chest strap device to obtain the hearts electrical signal. The use of the embodiment comprising a Metal Rubber membrane may also be used with any of the sensors described herein or with a combination of such sensor types.

Figures 9A, 9B:
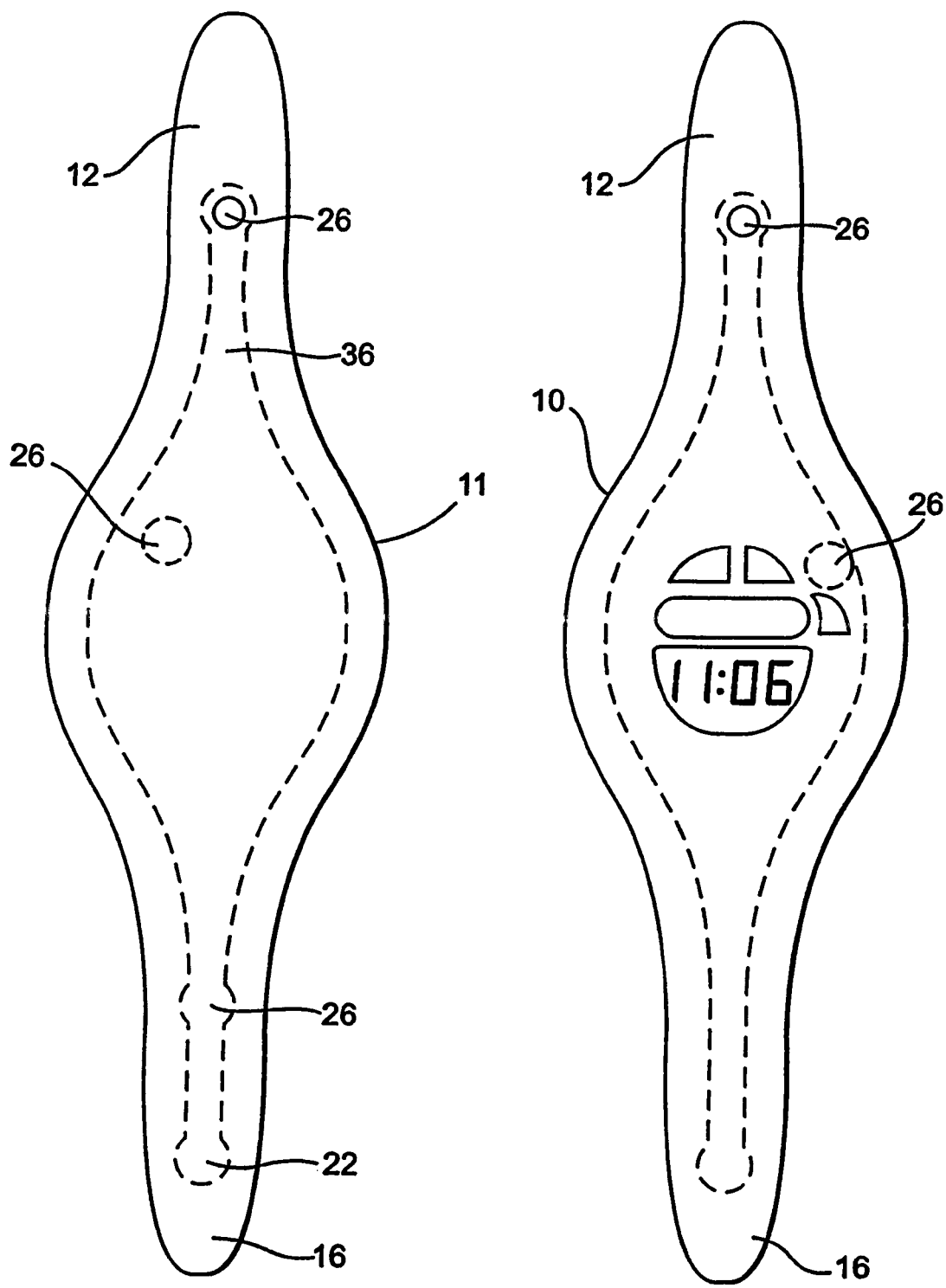
FIG. 9A is a bottom view illustrating placement of the alarm elements.
FIG. 9B is a top view illustrating placement of the alarm elements.

FIGS. 9A and 9B provide detail on the waking prompt 26 or alarm. The waking prompt 26 may be audible, silent through use of vibrations or emitted light. The vibrate alarm may be of the type described in either U.S. Pat. No. 4,456,387 or U.S. Pat. No. 5,400,301. The waking prompt 26 may also be partially housed in the pliable plastic insert 36 and housed in wristband B 12. Alternatively, the waking prompt 26 is housed in the monitor body 11. FIG. 8A illustrates housing the waking prompt in wristband A 16. Alternatively, the alarm unit may be housed in wristband A 16 using the pliable plastic insert 36. An audible or vibrational, or a combination thereof, alarm embodiment may be housed in the monitor body 11 or either wristband 12, 16 as discussed above.

Figure 10:
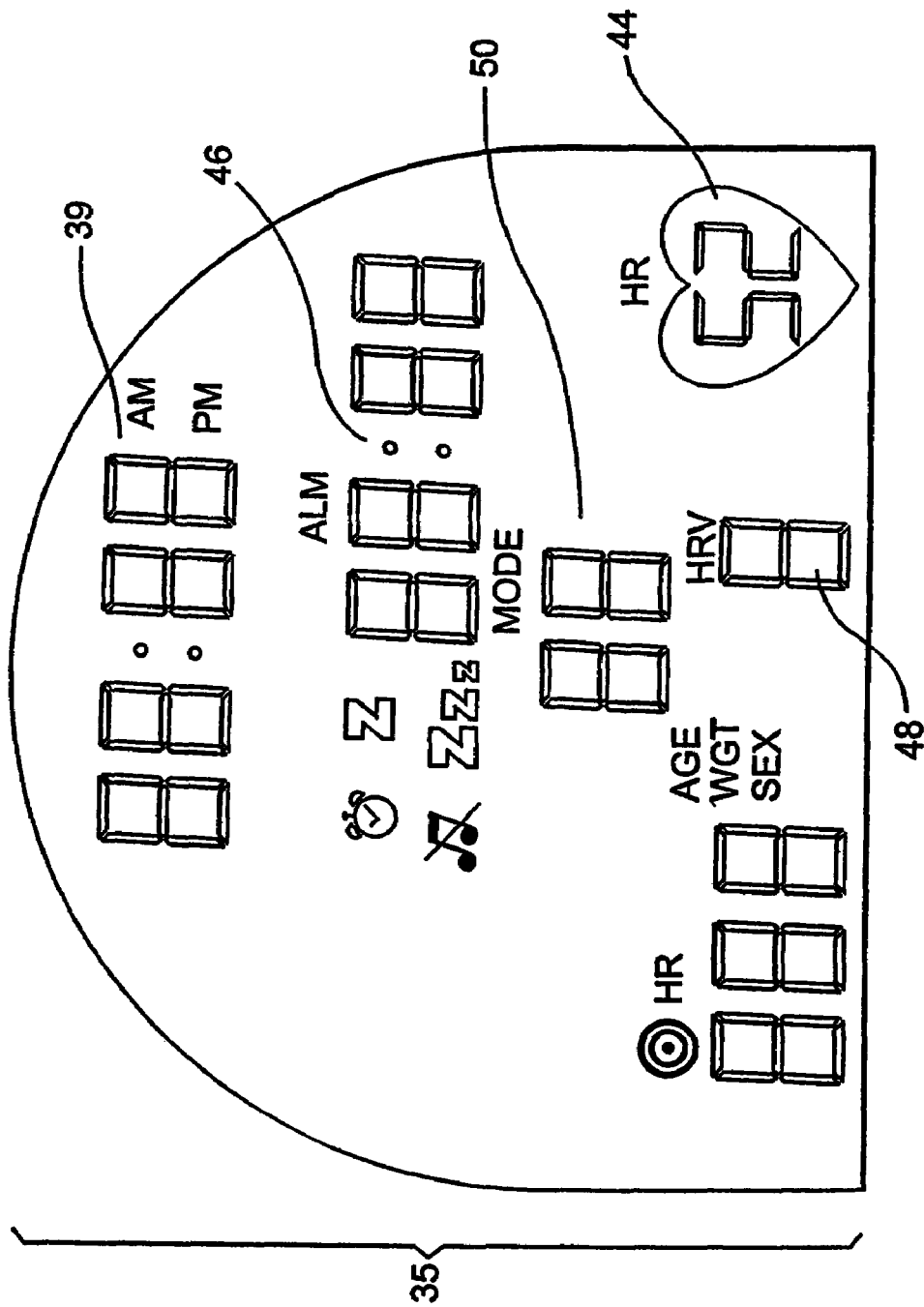
FIG. 10 is a view of one embodiment of the wrist worn monitor display.

Turning now to FIG. 10, a particular embodiment of the display 35 is illustrated. The monitor 10 will preferably generate an optical gauge or display 35. The display 35 will preferably assist the user to set the monitor 10 to the desired modes and functions. The attributes of the display 35 may include a running real time clock 39 and allow the user to view their heart rate 44, alarm settings 46, heart rate variability test results 48, recorded rest time results, and the mode of the monitor 50.

Figure 11:
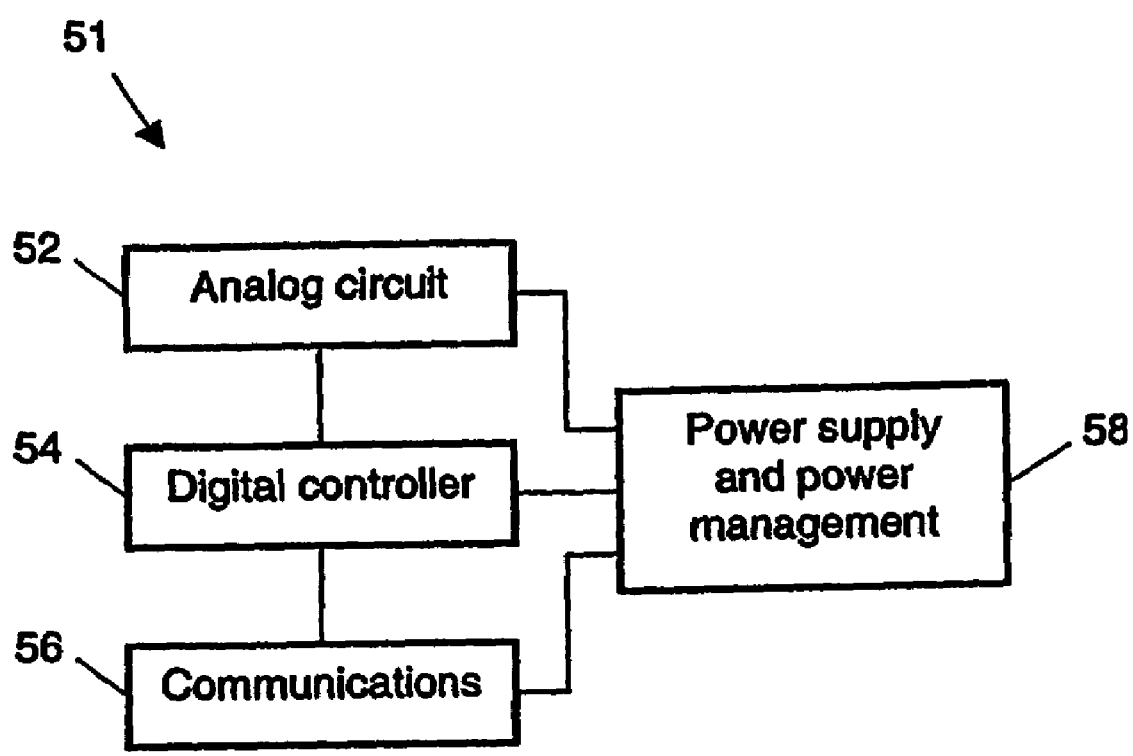
FIG. 11 is a block diagram of the circuitry.

The exterior of the inventive monitor having been described, embodiments of the internal circuitry will now be described. FIG. 11 provides a block diagram of the general circuitry blocks 51 and the interconnection thereof. The preferred embodiment thus provides an analog circuit block 52, a digital controller block 54, a communications block 56 and a power supply and power management block 58. Where, e.g., electrode sensors are employed, ECG (electrocardiograph) signals from the heart are monitored. With the use of the other sensors mentioned above used to obtain the heart rate, the information is used in a similar fashion and is known to those skilled in the art. The ECG signal is then conditioned to remove undesirable attributes, i.e., noise, from the signal. The analog signal is converted to a digital signal and then digitally processed under the software algorithms of the invention. The invention is capable of storing at least 24 hours of real time data. The details of the electronic circuitry are well known in the art and are not further described herein.

Figure 12:
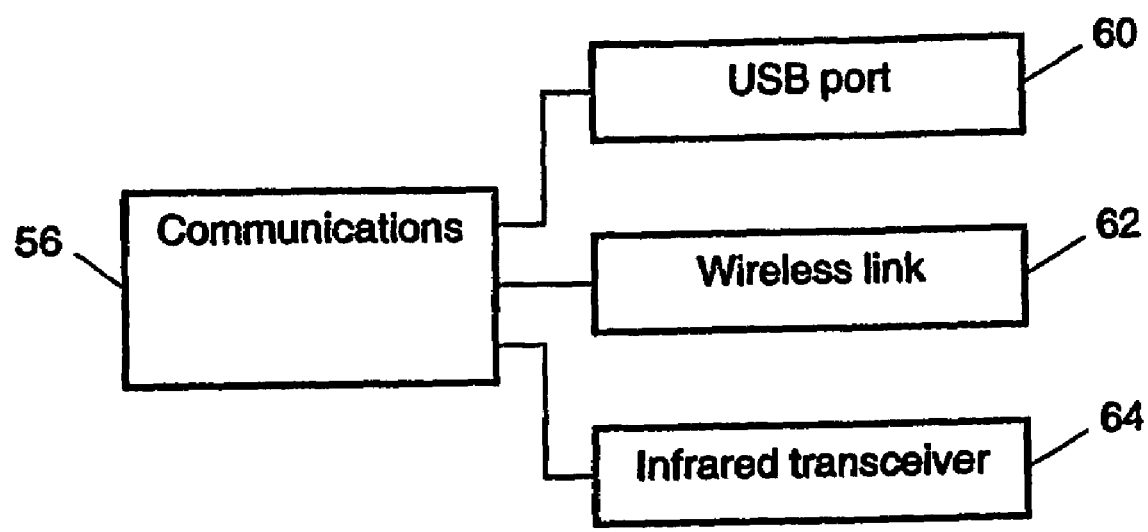
FIG. 12 is a block diagram of the communications unit with data transfer options.

FIG. 12 is a block diagram of the communications block 56 interconnected with different external communication methods. It is desirable and useful to be able to either store the acquired data internally within the device, externally or to transmit it to external devices or internal devices worn internally by the user. Exemplary internal devices include without limitation, defibrillation units and insulin pumps.

Therefore, it is contemplated that conventional, preferably high speed, communications with external and internal devices is an aspect of the present invention; it is contemplated that at least three types of transceivers may be used to accomplish this objective, each transceiver having different attributes and utility. For direct connection to a personal computer for further review, study and analysis of the data, or internal devices, high speed wired links are contemplated in the form of the direct connect USB 2.0 port 60. For ambulatory data transfer, wireless links are contemplated 62. For example, connection to a wireless communications devices, e.g., a Bluetooth® wireless device, may be provided. Alternatively, wireless USB 3.0 wireless ports or traditional USB ports are contemplated for exchanging the data. In addition, compatibility with certain medical instruments and notebook personal computers, an infrared transceiver 64 is provided as an alternate embodiment. The infrared method provides a slow, but proven and direct view optical link. Additional methods of transferring data from the inventive monitor will readily present themselves to those skilled in the art.

The hardware of various embodiments of the invention having been described, the operation of various embodiments of the invention will now be described.

Figure 13:
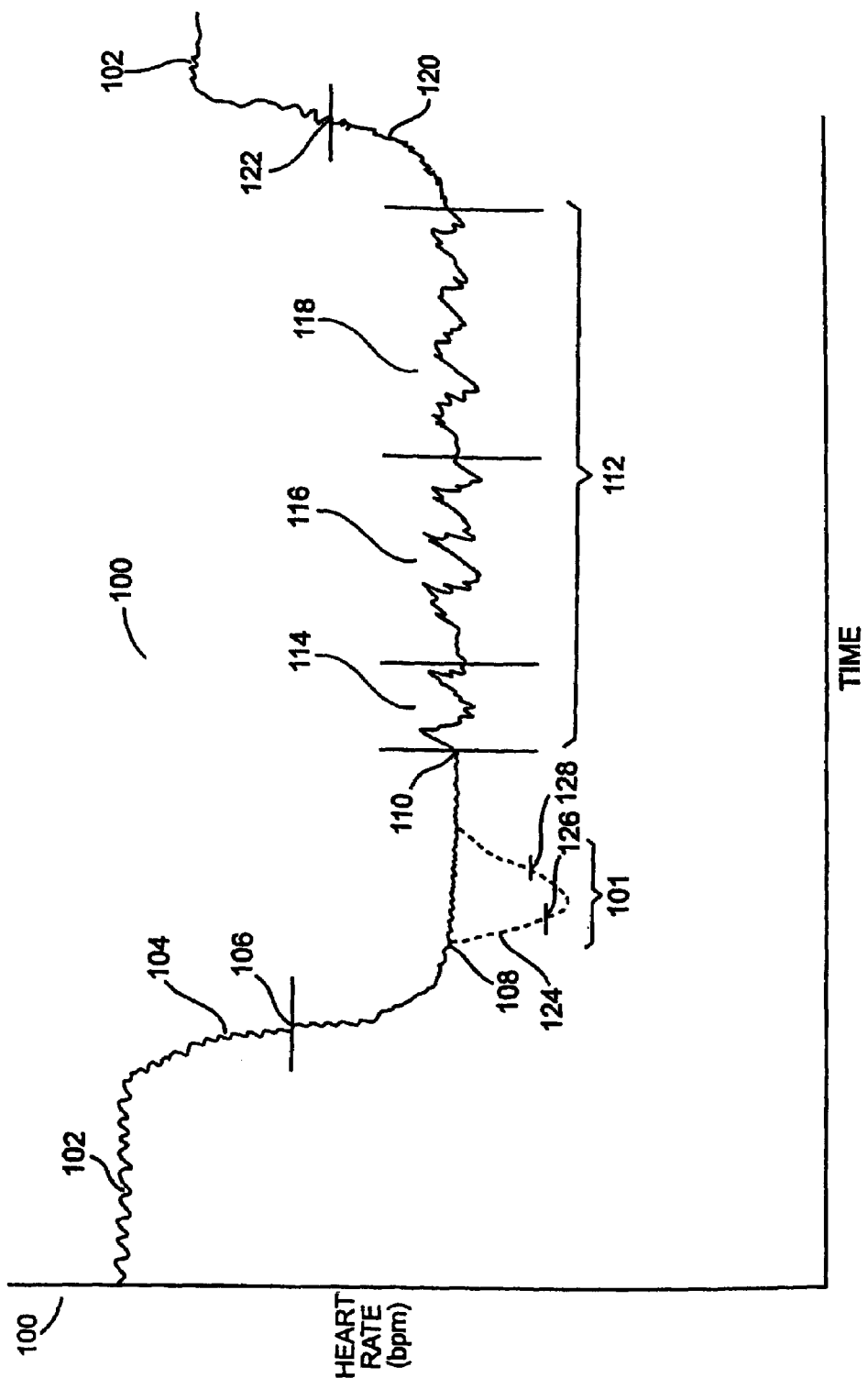
FIG. 13 is a graphical representation of the heart rate.

FIG. 13 illustrates typical heart rate variability 100 and includes typical heart rate data during a sleep apnea event in phantom 101. As discussed above, analysis of 24-hour HRV typically shows a nocturnal increase in the standard deviation of heart beat intervals. The heart rate and associated heart rate variability are essentially stable during the awake stage 102. The heart rate decreases significantly and rapidly 104 as the person begins to fall asleep. The heart rate eventually levels off, and the heart rate variability decreases, as a person eventually transitions 106 from the awake stage 102 to the non-REM stage 108. The heart rate variability remains relatively stable during the non-REM sleep stage 108.

As the individual eventually transitions from the non-REM sleep stage 108 to REM sleep 112, the heart rate becomes more erratic and the associated variability increases. There are several stages of REM sleep 112, each marked by changes in heart rate variability. FIG. 13 illustrates the first three REM stages, stage 1 114, stage 2 116, and stage 3 118. Typically, the first REM stage 114 lasts about 10 minutes, with each recurring REM stage 116, 118 lengthening, with the final stage lasting about one hour. The inventive monitor 10 is capable of detecting the heart rate variability within each sleep stage as well as the transition from one sleep stage to the next, i.e., the transition 106 from awake 102 to non-REM sleep 108, the transition 1010 from non-REM sleep 108 to REM sleep 112, and the completion of an REM sleep stage and subsequent transition to the next REM sleep stage.

Ultimately, the person exits REM sleep 112 and begins to awaken. This transition 122 is marked by an increase in heart rate 120 and is recognized by the monitor 10 when the heart rate increase passes a defined threshold 110, e.g., three standard deviations above the REM sleep state heart rate mean value. Eventually, the heart rate attains the stable awake stage 102 once more.

The heart rate data is processed in the digital processor component according to the computer program software code algorithms programmed therein. The essential theory of operation is that the heart rate data is first acquired by the monitor over a defined time interval. Typically at this stage, the user is in the awake state 102. The software then evaluates the heart rate itself and the variability of the interval between heart beats within a selected time period. Awake parameters are then calculated, comprising the mean awake heart rate value and standard deviation thereof. Alternatively, a heart rate threshold parameter may be entered by the user, corresponding to the user's resting heart rate, below which the user is recognized by the monitor as having fallen asleep. The user's heart rate, and associated variability, is next monitored and evaluated against the awake parameters, or the pre-entered threshold parameter, either periodically or continuously for significant changes. Specifically, the monitor is evaluating the user's heart rate for indication of the user's transition 106 from the awake state 102 to the non-REM sleep state 108. This transition 106 is marked by a decrease in heart rate 104 and is recognized by the device when the heart rate decrease passes a defined threshold 106, e.g., three standard deviations below the awake sleep state heart rate mean value. The threshold values of +/− three standard deviations from the local mean heart rate values are for illustrative purposes only. Those skilled in the art will readily comprehend that a number of threshold values may be used, depending on the particular user, etc.

As discussed above, the heart rate slows, and heart rate variability decreases when the user leaves the awake stage 102 and enters the non-REM sleep stage 108. Thus, when the awake-to-non-REM sleep threshold is reached 106, e.g., the user's heart rate drops below three standard deviations below the awake heart rate mean, the software recognizes this event as the user entering the non-REM sleep stage 108. Next, a new set of non-REM sleep parameters are calculated, including a mean non-REM heart rate and non-REM standard deviation over a defined time interval. The user's heart rate and associated variability is then monitored and evaluated against the non-REM sleep parameters, either periodically or continuously for significant changes.

The next event in the user's sleep cycle, assuming no interruptions in sleeping pattern, results in the user exiting non-REM sleep 108 and entering the first REM sleep stage or cycle 114. As described above, the transition from non-REM to REM sleep 110 results in an increase in the heart rate variability. Thus, when, e.g., the user's heart rate variability increases above a threshold level, e.g., the standard deviation about the mean increases by a factor of two as compared with the non-REM sleep standard deviation, the software recognizes this event as the user entering the REM sleep stage. Again, one skilled in the art will recognize that certain individuals may require a standard deviation factor increase that is either larger or smaller than a factor of two greater than the non-REM sleep standard deviation. A new set of REM sleep parameters are calculated, including an REM mean heart rate and an REM standard deviation over a defined time interval. The user's heart rate and associated variability is then monitored and evaluated against the REM sleep parameters, either periodically or continuously for significant changes.

Next, the user may exit REM sleep 112, in which case the heart rate increases significantly to cross a pre-defined threshold, e.g., more than three standard deviations over the mean REM sleep heart rate mean. The software is capable of recognizing on this basis that the user is now awake. The monitor is further capable of recognizing outlying data points resulting from transient events, e.g., the sleeping user physically changing positions, where the heart rate is temporarily increased, but rapidly returns to a level within the normal local deviation.

Alternatively, the user may exit the first REM sleep cycle 114, but instead of waking up will revert back to non-REM sleep 108 for a small amount of time and then enter the second, longer REM sleep cycle 116. The software is capable of recognizing the completion of one or more REM sleep cycles by differentially comparing the two sets of heart rate variability parameters. Ultimately, the user awakens and the heart rate increases such that the software recognizes the exit from REM sleep 112 and the awakened state. 122

Sleep apnea events may occur during either non-REM 108 or REM sleep 112 and are characterized by cessation of breathing and concomitant decrease in heart rate followed by an increase over the users normal heart rate, the heart rate should return to it's normal sleeping/resting heart rate after the event, although it may remain higher than normal, the users blood oxygen level will also fall off during the event. FIG. 13 illustrates the decrease in heart rate during non-REM sleep in phantom 101. The monitor is capable of detecting these apnea events when a pre-defined threshold is crossed by the user's heart rate, e.g., the user's heart rate decreases more than two standard deviations from the relevant sleep stage mean heart rate value over a defined time interval 126. One skilled in the art will readily recognize that the most appropriate time interval is dependent upon a number of factors known in the art. The monitor is further capable of recording the apnea event data for subsequent review by the user and/or a physician. For example, the user may wake to find that six apnea events occurred during the sleep period and use this information as a motivation to see his or her physician. An alternate embodiment provides a waking prompt that activates to bring the user out of the apnea event. The waking prompt 26 may be audio, visual, or vibratory. A further alternate embodiment provides remote transmission of the waking prompt to a 3$^{rd}$ person or remote device so that the 3$^{rd}$ person is alerted to the user's apnea event(s).

With this basic algorithmic theory in place for the software, many inventive applications present themselves.

Figure 14:
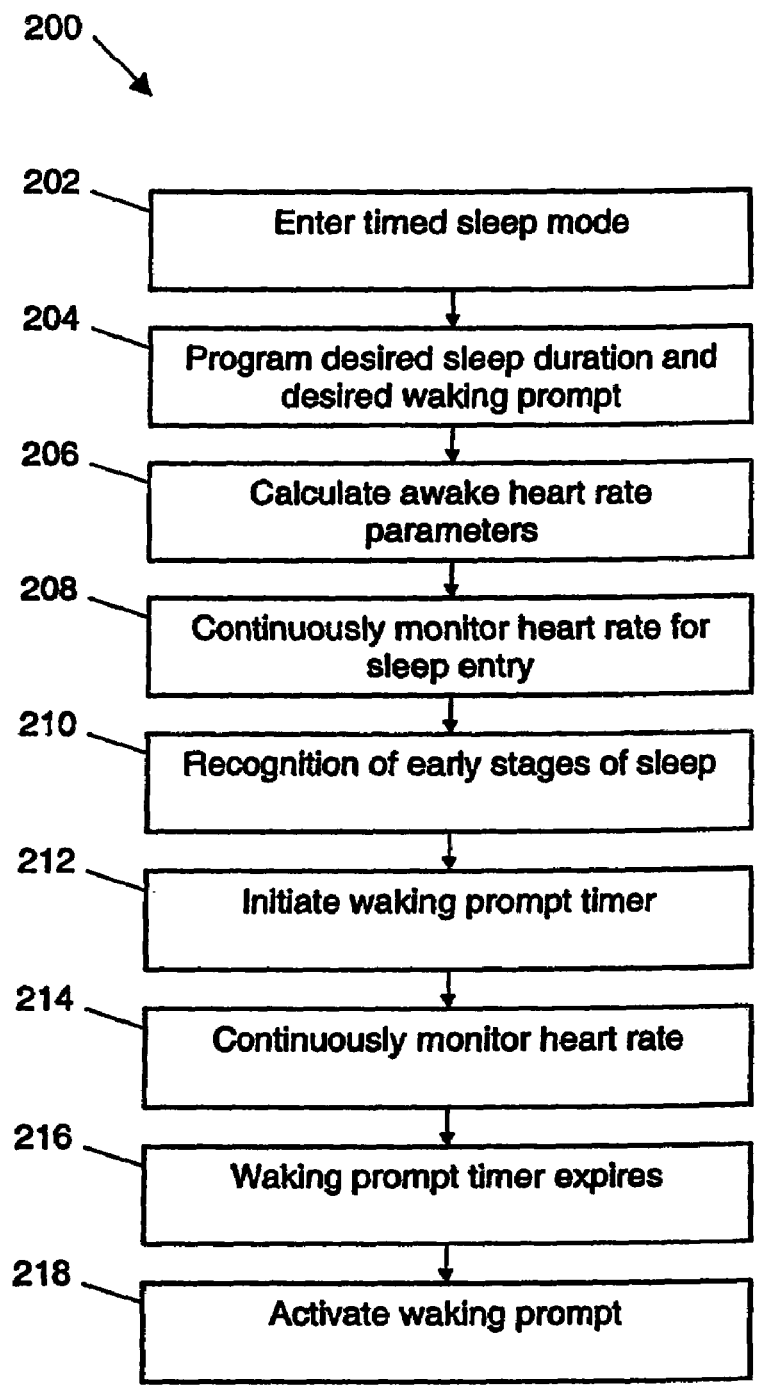
FIG. 14 is a flowchart for using the wrist worn monitor to take a timed and recorded nap of specified duration.

With specific reference to FIG. 14, the monitor is capable of allowing the user to take a nap of specified duration 200. The user selects timed-sleep mode 202 and enters the desired sleep duration and desired waking prompt 204. The waking prompt can be, as described above, either an audio, visual or vibrational alarm that is built into the monitor. The monitor acquires a signal of acceptable quality corresponding to the heart beat and begins to monitor for a particular time interval and ultimately calculates awake heart rate mean and standard deviation parameters 206. The preferred embodiment uses the above sensors to acquire the heart rate or ECG signals. The monitor then continuously, or periodically, monitors the heart rate for significant change, e.g., a 3 standard deviation decrease in heart rate from its local mean value, i.e., the awake mean in this case 208. When the monitor recognizes this change 210, it indicates that the user is now in the early stages of non-REM sleep and the waking prompt timer is started 212. The monitor then monitors and records the heart rate and associated variability 214 until either the user wakes and manually exits the selected mode or the waking prompt timer expires 216 which activates the waking prompt 218 and the heart rate monitoring is ended.

Figure 15:
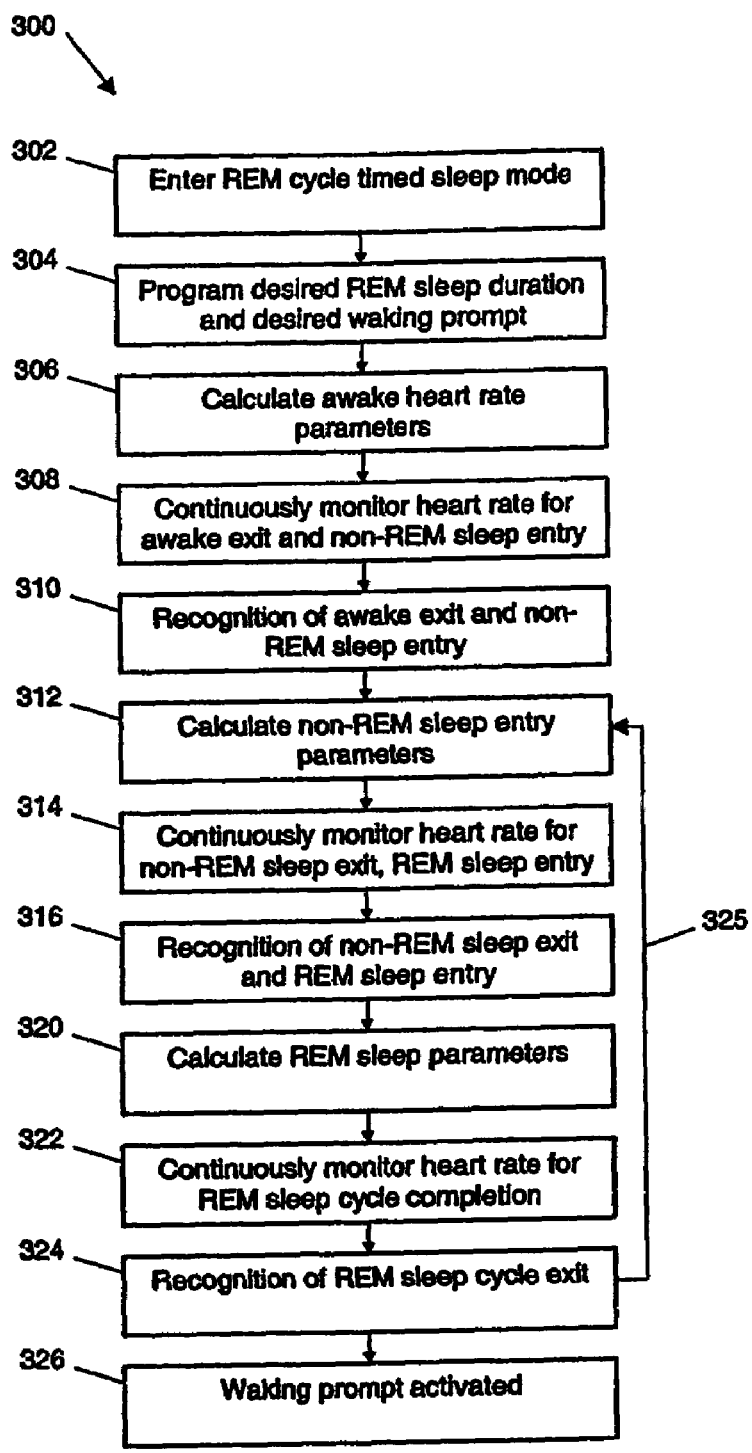
FIG. 15 is a flowchart for using the wrist worn monitor to take a timed and recorded nap with a specified duration in REM sleep stage.

The next inventive method 300 is illustrated in FIG. 15. Here, the monitor also allows the user to exit a nap at a specified point. The difference is that the duration is not specified, rather the user specifies that they wish to be awoken after one or more REM sleep stages or cycles are completed. Thus, the user enters the REM cycle timed sleep mode 302, awake heart rate parameters are calculated 306 and heart rate monitored for sleep entry 308 as above. When non-REM sleep is recognized 310, non-REM sleep heart rate parameters calculated 312 and monitored for REM sleep entry 314 as described above. When REM sleep is recognized 316, REM sleep heart rate parameters are calculated 320 and monitored for completion of the desired number of REM sleep stages or cycles 322. One or more REM sleep cycles may be monitored and completed under this operational mode using a looping algorithm 325. When the desired numbers of REM sleep cycles are completed 324 the waking prompt is activated 326 to wake the user.

Figure 16:
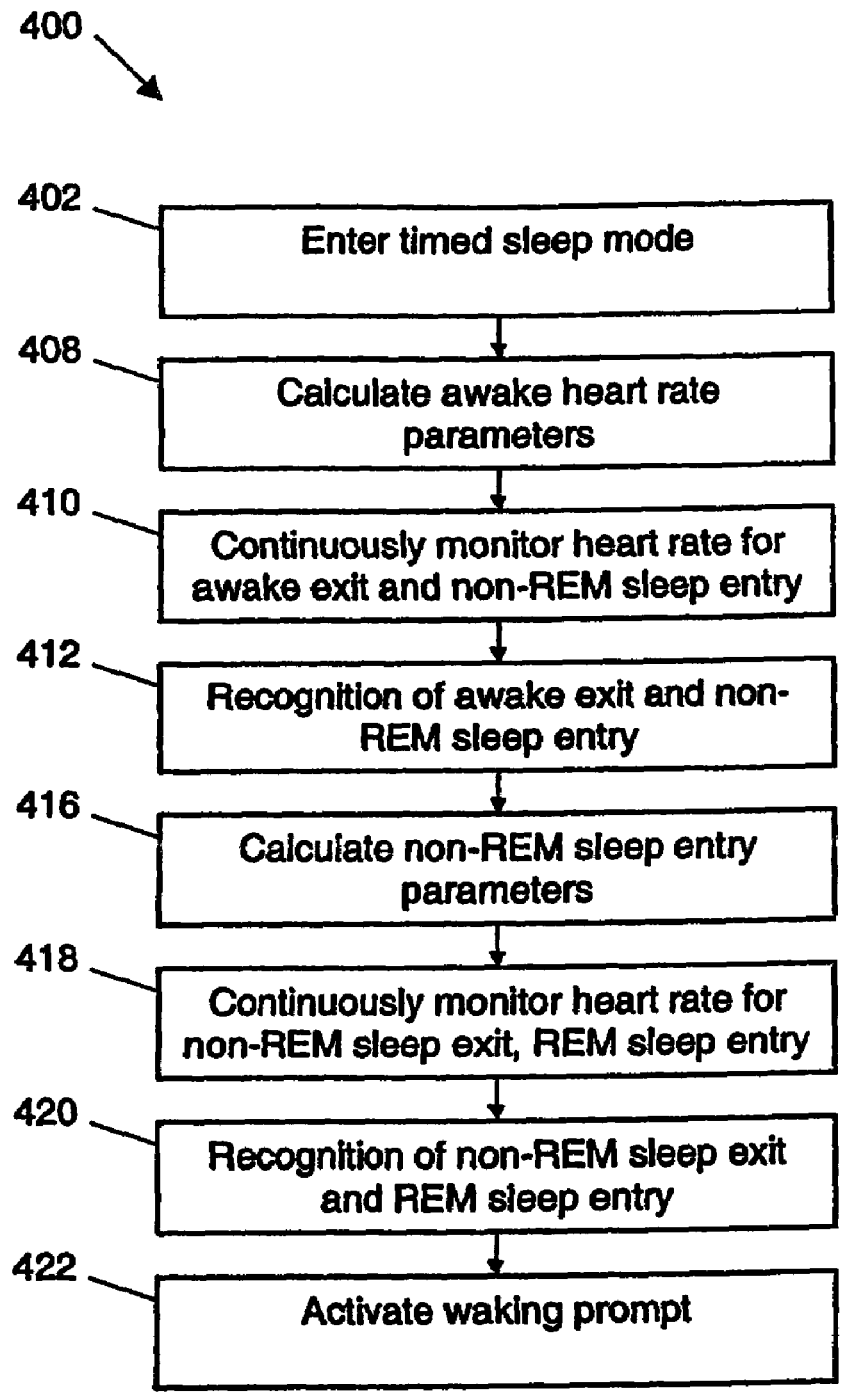
FIG. 16 is a flowchart for using the wrist worn monitor to take a timed and recorded nap with alarmed exit when REM sleep stage recognized.

A further modification of the duration limited nap is illustrated by FIG. 16. Here, the user desires to be awaked 400 in non-REM sleep or sleep stages one through four. Thus, the user enters timed sleep mode 402, the awake heart rate parameters are calculated 408 and monitored for non-REM sleep entry 410 as above. When non-REM sleep is recognized 412, non-REM sleep parameters are calculated 416 and monitored for non-REM sleep exit 418 as described above. When the monitor recognizes that the user is exiting non-REM sleep 420 the waking prompt is activated 422 to wake the user. The user may choose to be woken while they are in REM sleep or stage five sleep, this may be preferable because some individuals find it easier to get up within REM sleep. While others may choose to be woken in stage one, two, or three or four.

Still another embodiment provides a variation on the timed nap methods described above. In this embodiment, the heart rate variability data obtained through the inventive monitor may be used to determine when the user has achieved sleep or a beneficial level of rest. When the heart rate itself is lowered to a target resting heart rate level, the device may initiate an alarm to wake the user. Both the threshold target heart rate level and the duration of the sleep session may be determined by the user using input buttons to program the device. The user may also choose to be awoken by alarm before, during, or after specific sleep stages, such as REM or deep slow wave sleep.

Figure 17:
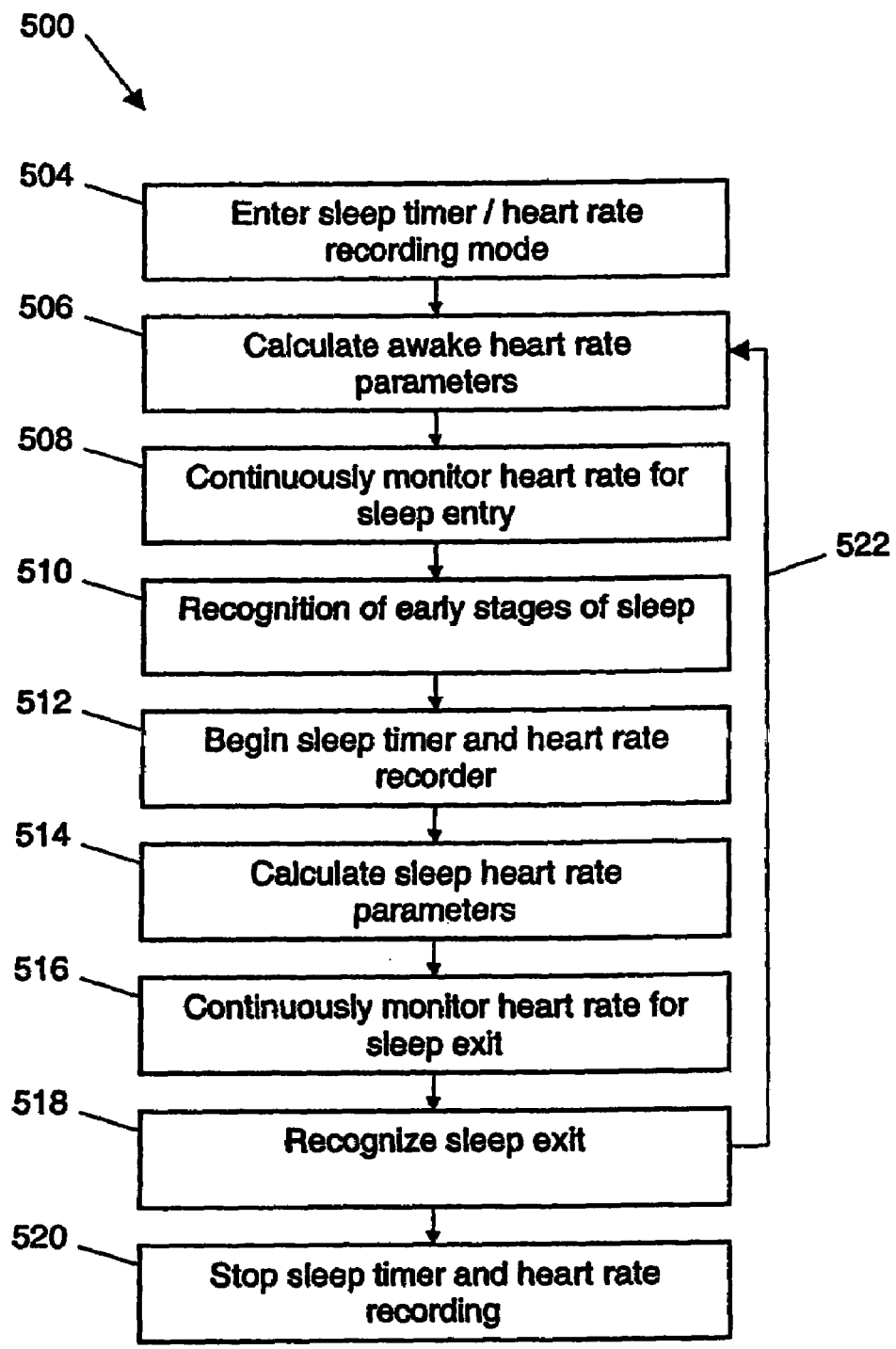
FIG. 17 is a flowchart for using the wrist worn monitor to record Heart Rate Variability and time to analyze sleep duration and quality.

FIG. 17 provides a method of monitoring both the duration and quality of a user's normal sleeping routine 500. In this mode, the user enters the sleep timer/heart rate recording mode 504, the awake heart rate parameters are calculated 506 and monitored for non-REM sleep entry 508 as above. Upon recognition of non-REM sleep entry 510, the sleep timer and heart rate and variability recorder are activated 512. Sleep heart rate parameters are calculated 514 and monitored 516 for sleep exit. When sleep exit is recognized 518, i.e., the user awakens, the sleep timer and recording of heart rate are stopped 520. In an alternate embodiment, a loop in the algorithm 522 allows for repeating of the previous logic steps in case the user awakens in the middle of the night and then falls asleep once more. This general recording of heart rate and variability thereof allows the user and/or physician to view the time-stamped events of the night for sleep duration and quality, i.e., time spent in non-REM and/or the REM sleep stages or cycles with the ability to view sleep interruption events.

Figure 18:
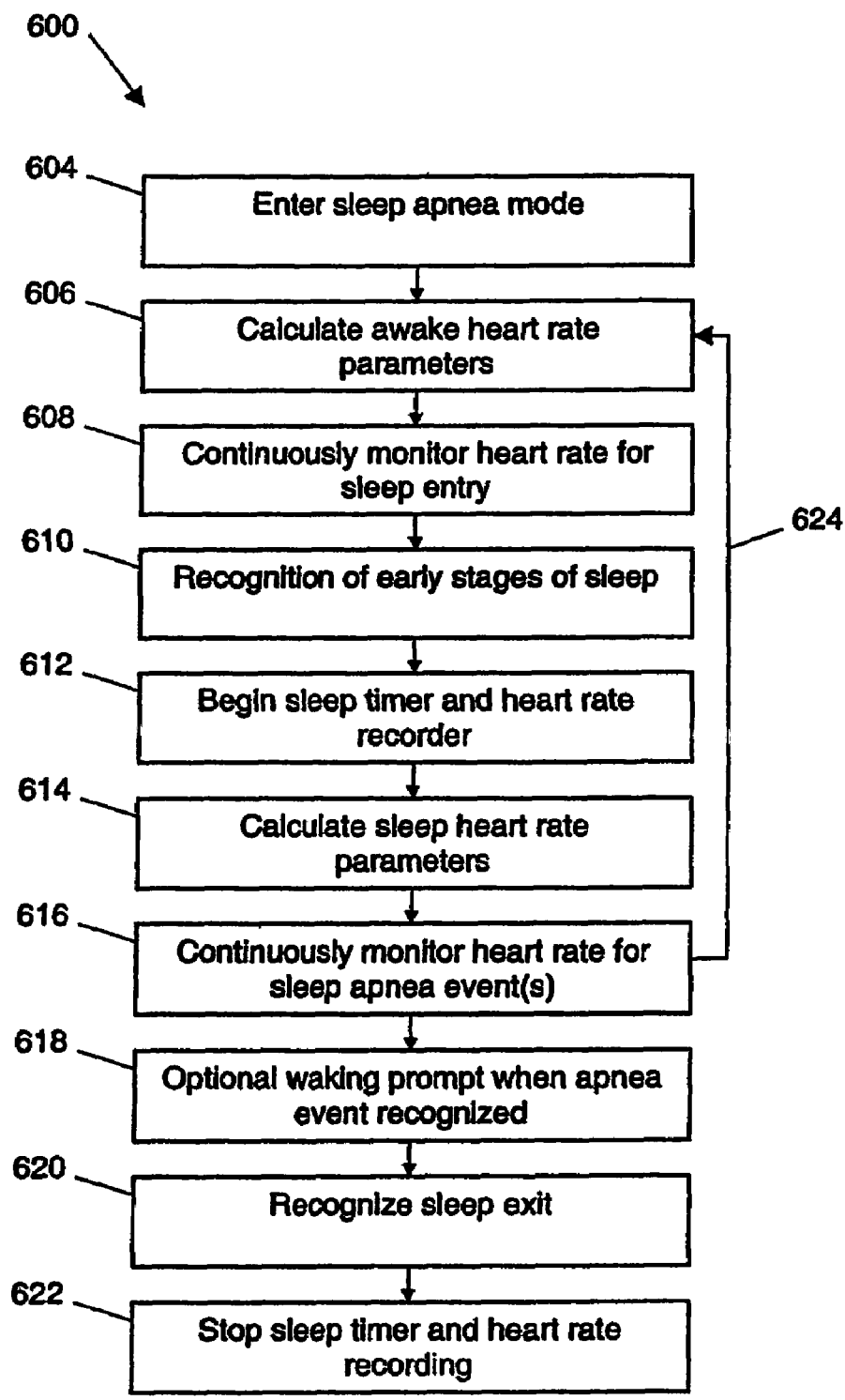
FIG. 18 is a flowchart for using the wrist worn monitor to monitor for and record Heart Rate Variability for sleep apnea events.

Turning now to FIG. 18, the monitor is used to detect sleep apnea events 600. In this case, the user enters sleep apnea monitoring mode 604, the awake heart rate parameters are calculated 606 and monitored 608 for sleep entry as above. Once sleep entry is recognized 610, the sleep timer and heart rate recorder are prompted to begin 612. Sleep heart rate parameters, including the stages for non-REM and REM sleep stages, are calculated 614 and monitored 616 as above. The monitor is, in this case, monitoring for deviations below the sleep heart rate parameters which are diagnostic of sleep apnea events 101 as indicated in FIG. 12. The intent of this inventive method is to record the apnea events for later review by the user and/or physician to assist in diagnosing sleep apnea and to assist in monitoring the effectiveness of treatment options. The monitor has the capability, in the preferred embodiment, to stop the sleep timer and heart rate recording 622 when sleep exit is recognized 620 and, as above, restart the timer and recording if the user falls back asleep as illustrated by the looping algorithm 624. This capability is particularly important if the apnea event causes the user to come out of the sleep state. As discussed above, alternate embodiments include a waking prompt 618, either audio, visual or vibratory, that will wake the user upon detection of an apnea event. Alternatively, an alarm signal may be transmitted to a 3$^{rd}$ person alerting them of the user's apnea event(s). Finally, the number of apnea events may be displayed for the user, thus providing motivation to see their physician.

Figure 19:
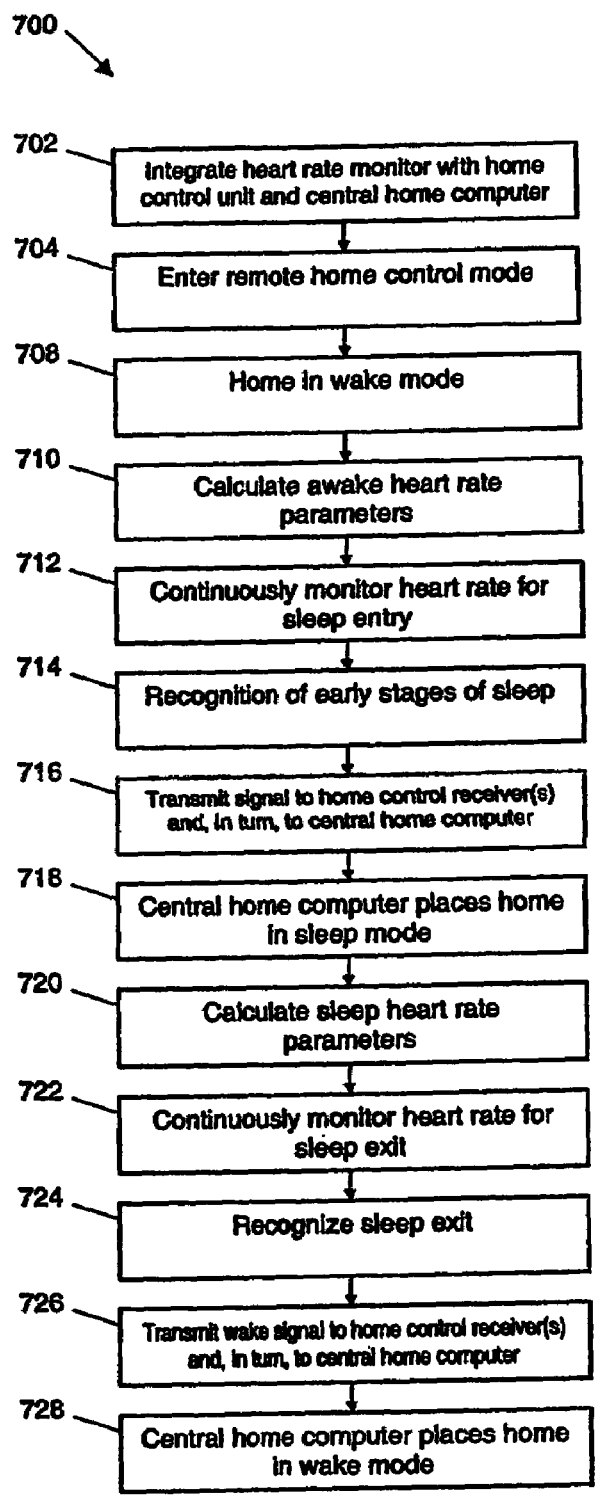
FIG. 19 is a flowchart for sending the heart rate variability data obtained by the wrist worn monitor to a central home computer to place the home in "sleep" and "awake" modes.

FIG. 19 illustrates one embodiment of the monitor's ability to assist in controlling a home's functional features based on heart rate variability 700. In this embodiment, the monitor is used in concert with a home's electronics control unit 702. Many homes are equipped with a controlling computer system. These homes have been referred to as 'smart houses.' The home's controlling computer or electronics control unit manages the functions of the home. These functions may include: television; personal computer; shower; home security system; lights; kitchen appliances; garage door and other functional features of a home. This invention is capable of working in concert with the home's controlling computer system and works to synchronize the home's functions with the homeowner's functions. The user enters remote home control mode 704 and, with the home in 'wake' mode 708, wears the device before bed. The awake parameters are calculated 710 and monitored 712 as above. When sleep is recognized as discussed above 714, the wrist worn monitor sends out a signal to the home's controlling computer via a home control receiver(s) 716, which then prepares the home for the night, i.e., places the home in 'sleep' mode 718. This may comprise functions such as shutting lights and televisions off, ensuring the garage door is down, setting the thermostat at an appropriate temperature for the night, etc. The opposite is done in the morning. Thus, the sleeping user's heart rate parameters are calculated as above 720 and monitored 722 for sleep exit 724. When the user's heart rate level and variability rises above the threshold level, i.e., sleep exit is recognized 724, the monitor sends a signal to the central home computer via the home control receiver(s) 726 to prepare the home for the day, i.e., placing the home in 'awake' mode 728. Thus, functions such as turning on the lights, shower, coffee maker, alarm are accomplished. In addition to using the heart rate variability of the user to control the features of the home, the monitor may have a button that manually accomplishes the tasks without use of heart rate variability information.

Figure 20:
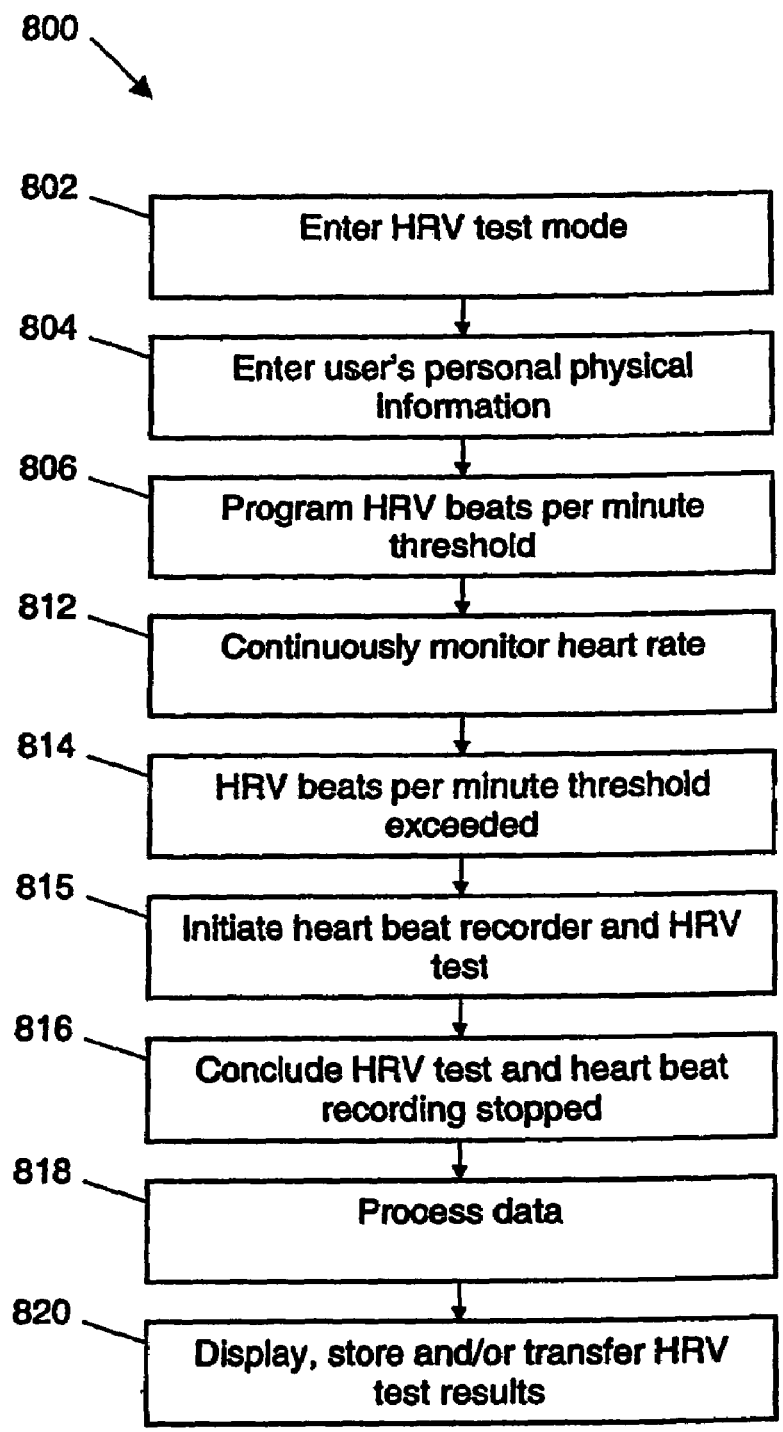
FIG. 20 is a flowchart for using the wrist worn monitor to perform a Heart Rate Variability (HRV) test.

FIG. 20 provides another application of the invention. A heart rate variability test may be taken by the monitor 800. Here, the user enters the HRV testing mode 802 and then enters personal physical information 804 which may affect the test results such as age, sex, weight. A target heart rate threshold is entered by the user and desired duration of the test 806. The target heart rate threshold may be either an upper or lower threshold. The test may be administered either while the user is at rest, while the user sleeps, either in non-REM sleep stage only or in REM sleep stage only or across both sleep stages, or during physical activity. The monitor then monitors the heart rate 812 until the target lower threshold is crossed which either indicates that the user has attained a resting level or, alternatively, has entered the non-REM sleep stage, or, if the monitor is used in connection with physical activity, an upper target heart rate threshold is utilized. In either case, the monitor initiates the heart beat recorder and the HRV test commences 815 for a specified time once the target heart rate threshold is crossed 814. The longer the HRV test, the more accurate the results will be. When the specified duration is reached, the HRV test concludes 816 and the monitor then processes the data 818. The data is preferably displayed on a scale of 1-200 to indicate the quality of the user's HRV 820. Alternatively, a scale from 1-10 may be used or letters, e.g., A, B, C, etc., or even colors like green (good HRV), yellow (marginal HRV), red (poor HRV) may be used.

Figure 21:
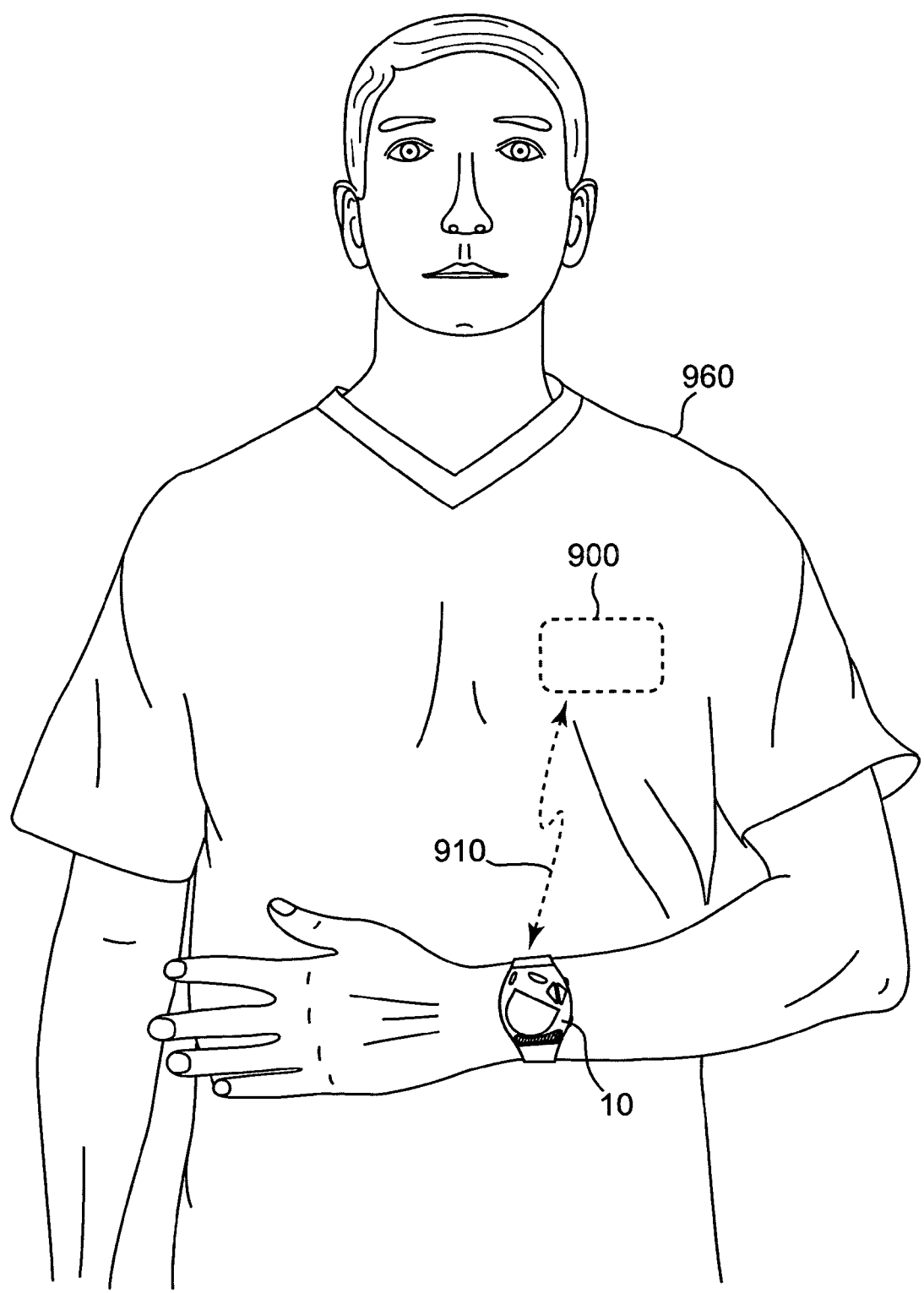
FIG. 21 illustrates a user with the wrist worn monitor and an internal device.

FIG. 21 illustrates a user 960 with an internal device 900 and the inventive device 10. As described above in relation to FIGS. 11 and 12, the internal device may transmit data that is received by the inventive device's transceiver. In turn, the user may utilize the inventive monitor's transceiver to transmit data to the internal device. This two-way communication is illustrated by the two-headed arrow 910.

Figure 22:
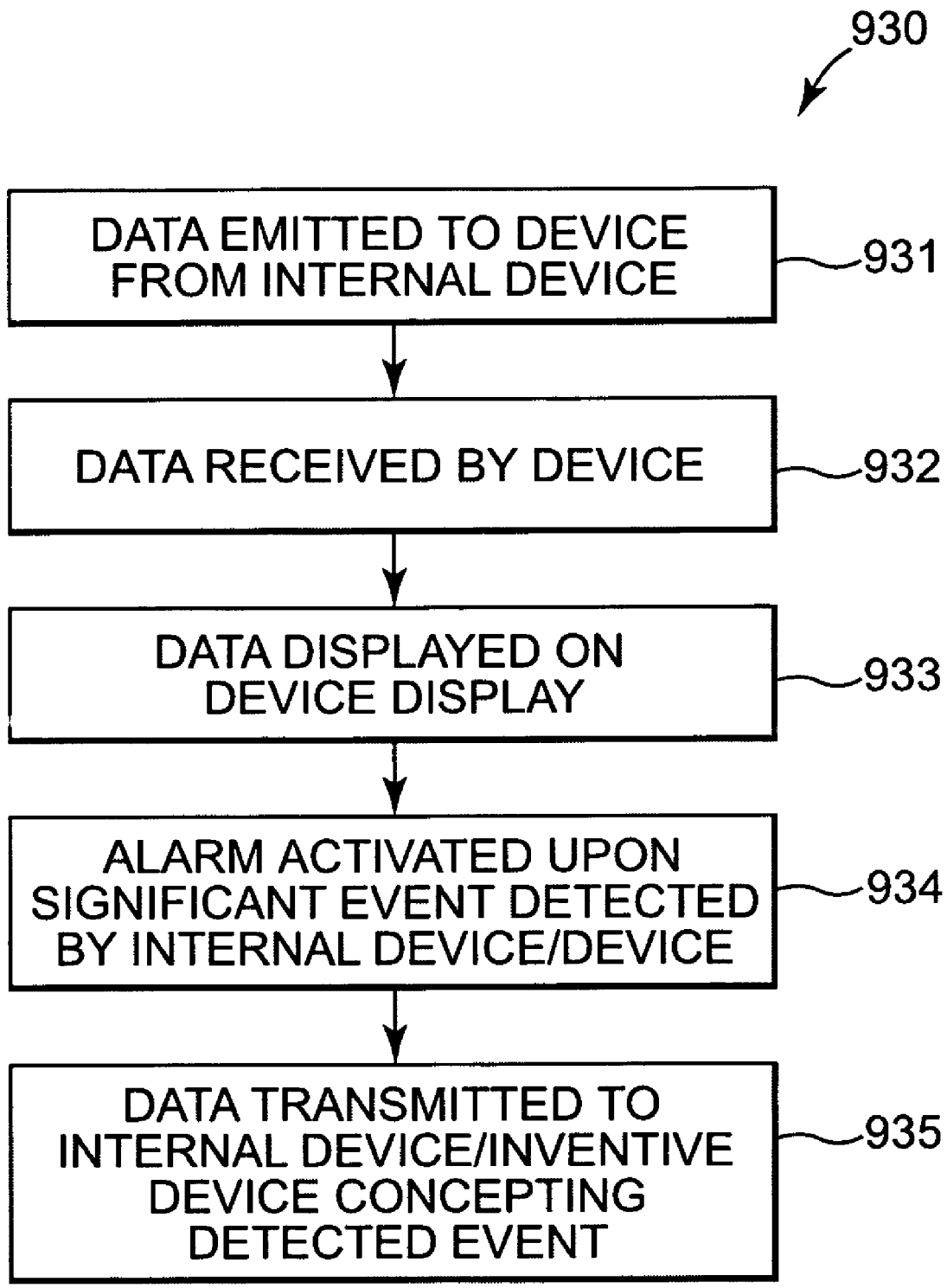
FIG. 22 is a flowchart for using the wrist worn monitor to exchange data with an internal device.

FIG. 22 illustrates an inventive method 930. The inventive device communicates with an internal device. The internal device emits a signal to the inventive device 931, the signal is received and evaluated by the inventive device 932. The information may be displayed on the inventive device display 933. Certain "significant events" may warrant the immediate attention of the user, in this case the inventive device's audio or vibrate alarm will be activated 934, the communication that warranted the alarm activation will be displayed on the inventive devices display. The alarmed event may be detected by the inventive device or the internal device, in this case the event information will be transmitted to the device that did not detect the event 935, for example if the inventive device detected the event it will share it with the internal device and if the internal device detected the event it will share it with the inventive device. The data transmissions or communications are stored in the inventive devices memory as well as the internal devices memory where they can be transmitted to physicians, personal computers or displayed on the inventive devices display.

Figure 23:
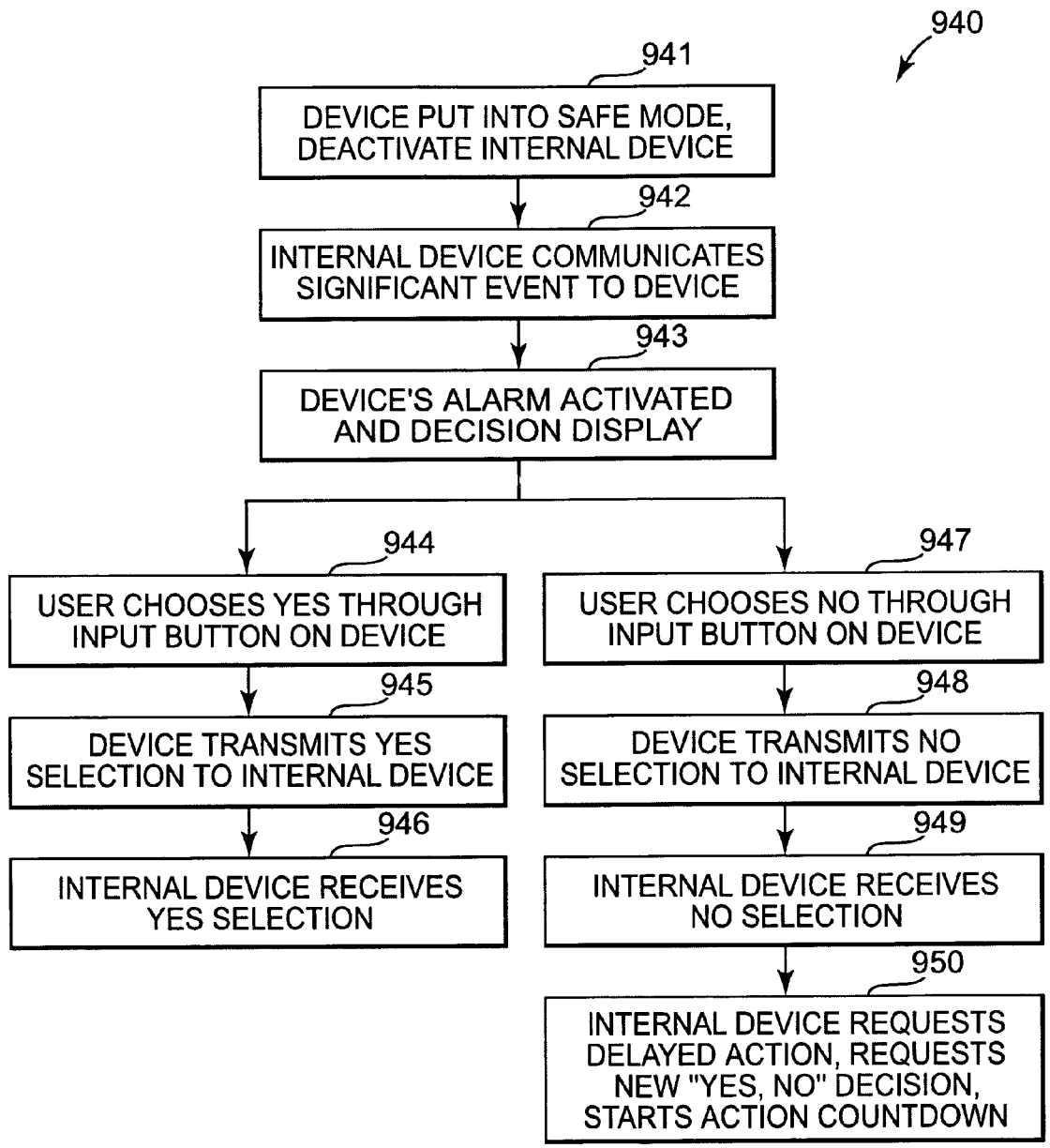
FIG. 23 is a flowchart for using the wrist worn monitor to communicate and give commands to an internal device.

FIG. 23 illustrates an additional method of communication between the inventive device and an internal device 940. Some internal devices take actions that directly effect its user and will effect them physically and mentally. Some of the actions taken by internal devices may out its user at risk in certain situations. For example, if a pain drug is administered via an internal device while its user is rock climbing the effects of the drug may have adverse effects on the users mental and physical abilities that are needed to perform the tasks involved with rock climbing and may put the user in danger. The internal device's actions (drug delivery, defibrillation, insulin delivery) can be deactivated via the inventive devices input buttons or put into a safe mode 941. The safe mode is used when the user is in a situation that could become dangerous if their internal device takes action, or takes action without their knowledge, or prior knowledge. The user may choose to deactivate actions taken by the internal device until reactivated, this can be accomplished by using the inventive devices input buttons, the inventive device or internal device may alert the user at predetermined time intervals to remind them that the internal devices actions have been deactivated and ask them to reactivate the internal devices action process. The internal device transmits or communicates a significant event to the inventive device 942. A significant event is an event that warrants action taken by the internal device, e.g., an impending defibrillation stimulation or insulation dosage. The inventive device receives the internal device's transmission and activates the alarm (audio/vibrate) and the monitor may prompt the user to make a decision concerning the pending action 943. The inventive devices display may display a question such as, 'I.D. Action Request Take Action? Yes No', the specific action to be taken by the internal device may also be displayed on the inventive devices display. The actual language displayed on the inventive devices may vary but will make it clear to the user that the internal device is requesting to take action or that impending action will take place. If the user chooses to accept the internal devices request to perform an action they utilize the appropriate input button and chooses 'yes' 944. The inventive device transmits the 'yes' selection to the internal device 945. The internal device receives the transmission from the inventive device and takes the appropriate action 946. If the user chooses not to accept the internal devices request to perform an action they utilize the appropriate input button and chooses 'no' 947. The inventive device transmits the 'no' selection to the internal device 948. The internal device receives the transmission from the inventive device and takes the appropriate action 949, which in this case is no action. While the user has chosen to not have any action performed by the internal device, the internal device can override this request by the user if circumstances require, this override may take place without alarming the user, even in 'safe mode', may take place during the 'safe mode' communication process, or may simply delay the action taken by the internal device while still alerting the user to an impending action form the internal device via the inventive device (display, alarm) in the event of a delay a timed countdown may be displayed on the inventive devices display signifying the amount of time before action is taken by the internal device 950.

Figure 24:
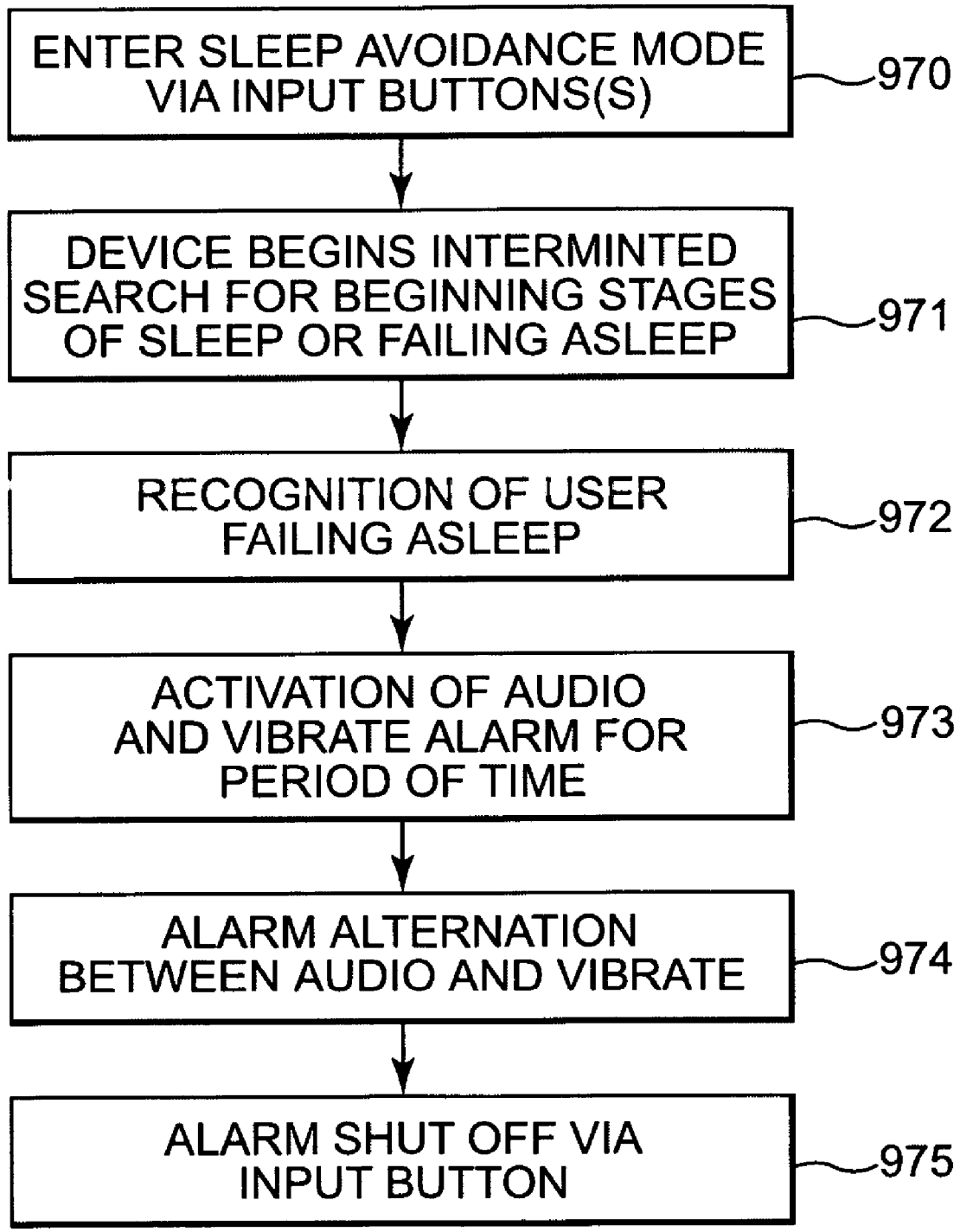
FIG. 24 is a flow chart for using the wrist worn monitor for 'sleep avoidance'.

FIG. 24 is a flow chart for using the wrist worn monitor for 'sleep avoidance'. The user enters 'sleep avoidance' mode using an input button(s) 970. The device begins searching for the onset of sleep 971 using the integrated processor. This search may be a continuous search or may be a timed intermittent search. The device's processor may recognize the onset of sleep 972, or the beginning stages of sleep based on HRV data. When the monitor's processor recognizes the HRV data patterns associated with sleep onset, the audio and vibrate alarms are activated 973. The alarm may remain activated for a predetermined amount of time, after this time has expired the alarms may alternate between audio and vibrate as a fail safe 974. The alternation of the alarms may be swift so the user is woken quickly but not in a rhythmic fashion so as to create an irritating situation to wake the user. The alarm may be shut off via input button(s) 975, to ensure that the user is awake and cognizant. The alarm may be shut off before the fail-safe operation is activated within the predetermined amount of time.

The monitor further provides the capability, through use of selective input of operational modes, performance of one or more of the above-described functions in parallel, at the same time, during a single monitoring session.

The above specification describes certain preferred embodiments of this invention. This specification is in no way intended to limit the scope of the claims. Other modifications, alterations, or substitutions may now suggest themselves to those skilled in the art, all of which are within the spirit and scope of the present invention. It is therefore intended that the present invention be limited only by the scope of the attached claims below:

The invention claimed is:

1. A wrist or arm worn heart rate variability monitor, comprising:
   at least one sensor embedded in a membrane for detecting heart rate signals generated within a body when placed in contact with the body's wrist, wherein the sensor is capable of monitoring signals selected from the group consisting of optical, infra-red, pressure, ultrasonic and electrical signals;
   a circuit that conditions the electrical signals and converts the analog signals to digital signal data;
   a heart rate variability signal processor that monitors and analyzes the digital signal data, calculates parameters comprising the mean digital signal value and at least one standard deviation of the digital signal data monitored and establishes a threshold level based on the calculated parameters evaluated when the user is in an awake state and just prior to real-time heart rate variability data monitoring, wherein the calculated threshold level is neither predetermined nor preset and does reflect the user's actual heart rate and heart rate variability over the defined time interval, and wherein the processor monitors the digital signal data and recognizes the crossing of the established threshold level by the digital signal data and may be programmed to establish a new threshold level into a subsequent sleep state that reflects the body's actual heart rate and heart rate variability within the subsequent sleep state and then performs at least one HRV test using the new threshold level while the body is within the subsequent sleep state and then continues to monitor the body's HRV for additional threshold crossings;
   an alarm that may be activated to alert the user of abnormal conditions or events or the crossing of a specified threshold level by the heart rate variability; and
   a memory capable of storing the established threshold levels and real time digital signal data.

2. The heart rate variability monitor of claim 1, wherein the at least one sensor comprises at least one piezoelectric sensor.

3. The heart rate variability monitor of claim 1, further wherein the at least one sensor comprises at least one micro electromechanical sensor.

4. The heart rate variability monitor of claim 1, further comprising the at least one sensor being selected from the group consisting of electrode sensors, optical sensors, cMUT sensors and piezoelectric sensors.

5. The heart rate variability monitor of claim 1, further comprising:
   a transceiver for two-way communication with an internal device, wherein the alarm may be activated upon communication of a significant event to the transceiver by the internal device.

6. The heart rate variability monitor of claim 5, wherein the internal device communicates diagnostic data to the heart rate variability monitor.

7. The heart rate variability monitor of claim 5, further comprising communicating to the internal device that the significant event is permitted to occur, not permitted to occur, or permitted to occur but only after a period of time has passed.

8. The heart rate variability monitor of claim 5, wherein the internal device is a defibrillator and the significant event comprises defibrillation.

9. The heart rate variability monitor of claim 5, wherein the internal device is a drug delivery system and the significant event comprises delivery of the drug.

10. The heart rate variability monitor of claim 9, wherein the drug delivery system comprises an insulin pump and the significant event comprises delivery of insulin.

11. The heart rate variability monitor of claim 1, wherein the processor is capable of analyzing HRV data to determine when the user is entering the beginning stages of sleep and activating the alarm to ensure the user remains awake.

12. The heart rate variability monitor of claim 4, further comprising the monitor having a back surface; and a conductive membrane comprising metal rubber disposed on the back surface of the monitor and contacting the at least one sensor and further having contact with the user's skin.

13. The heart rate variability monitor of claim 4, further comprising an infra-red sensor, wherein the infra-red sensor monitors heart rate variability.

14. The heart rate variability monitor of claim 1, wherein the processor is capable of using the infra-red and/or optical signals to perform pulse oximetry analysis.

15. The heart rate variability monitor of claim 1, wherein the at least one sensor monitors blood oxygen levels to assist in diagnosing, monitoring or treating diseases, conditions or maladies.

16. The heart rate variability monitor of claim 1, further comprising a memory device.

* * * * *